(12) United States Patent
Jewett et al.

(10) Patent No.: US 10,047,061 B2
(45) Date of Patent: *Aug. 14, 2018

(54) WATER-SOLUBLE TRIAZABUTADIENES

(71) Applicant: Arizona Board of Regents on Behalf of The University of Arizona, Tucson, AZ (US)

(72) Inventors: John C. Jewett, Tucson, AZ (US); Flora W. Kimani, Tucson, AZ (US)

(73) Assignee: Arizona Board of Regents on Behalf of The University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,894
(22) PCT Filed: Jun. 10, 2015
(86) PCT No.: PCT/US2015/035136
§ 371 (c)(1),
(2) Date: Dec. 9, 2016

(87) PCT Pub. No.: WO2015/191735
PCT Pub. Date: Dec. 17, 2015

(65) Prior Publication Data
US 2017/0114033 A1    Apr. 27, 2017

Related U.S. Application Data

(60) Provisional application No. 62/128,707, filed on Mar. 5, 2015, provisional application No. 62/114,735, filed on Feb. 11, 2015, provisional application No. 62/109,170, filed on Jan. 29, 2015, provisional application No. 62/010,861, filed on Jun. 11, 2014.

(51) Int. Cl.
| | |
|---|---|
| *C07D 233/88* | (2006.01) |
| *C07D 277/82* | (2006.01) |
| *C07C 245/06* | (2006.01) |
| *C07D 233/70* | (2006.01) |
| *C07D 277/50* | (2006.01) |
| *C07D 235/30* | (2006.01) |
| *C07D 403/12* | (2006.01) |
| *C09J 11/06* | (2006.01) |
| *C09J 201/06* | (2006.01) |
| *G01N 33/68* | (2006.01) |
| *C09B 43/00* | (2006.01) |

(52) U.S. Cl.
CPC .......... *C07D 277/82* (2013.01); *C07C 245/06* (2013.01); *C07D 233/70* (2013.01); *C07D 233/88* (2013.01); *C07D 235/30* (2013.01); *C07D 277/50* (2013.01); *C07D 403/12* (2013.01); *C09B 43/00* (2013.01); *C09J 11/06* (2013.01); *C09J 201/06* (2013.01); *G01N 33/6845* (2013.01); *C09J 2201/614* (2013.01)

(58) Field of Classification Search
CPC .. C07D 277/82; C07D 233/70; C07D 233/88; C07D 235/30; C07D 277/50; C07D 403/12; C07C 245/06; C09B 43/00; C09J 11/06; C09J 201/06; C09J 2201/614; G01N 33/6845

See application file for complete search history.

(56) References Cited

U.S. PATENT DOCUMENTS

| | | | |
|---|---|---|---|
| 3,591,575 A | 7/1971 | Golda | |
| 3,607,542 A | 9/1971 | George et al. | |
| 3,959,210 A | 5/1976 | Lipatova et al. | |
| 4,107,353 A | 8/1978 | Gabriel et al. | |
| 4,218,279 A | 8/1980 | Green | |
| 4,356,050 A | 10/1982 | Crivello et al. | |
| 4,602,073 A | 7/1986 | Skoultchi et al. | |
| 5,856,373 A | 1/1999 | Kaisaki et al. | |
| 8,603,451 B2 | 12/2013 | Zhang et al. | |
| 8,617,827 B2 | 12/2013 | Hell et al. | |
| 9,458,143 B1 | 10/2016 | Jewett et al. | |
| 9,593,080 B1 | 3/2017 | Jewett et al. | |
| 2002/0197439 A1 | 12/2002 | Berneth et al. | |
| 2004/0241205 A1 | 12/2004 | Babich et al. | |
| 2005/0080260 A1 | 4/2005 | Mills et al. | |
| 2007/0049587 A1 | 3/2007 | Zbinden et al. | |

(Continued)

FOREIGN PATENT DOCUMENTS

| | | |
|---|---|---|
| DE | 265008 A1 | 2/1989 |
| DE | 4242428 A1 | 10/1993 |

(Continued)

OTHER PUBLICATIONS

Kimani and Jewett, 2015, Angewandte Chemie International Edition (DOI: 10.1002/anie.201411277—Online ahead of print).
Zhong et al., 2014, Nature Nanotechnology 9, 858-866.
Stewart et al., 2011, J Polym Sci B Polym Phys 49(11):757-771.
Poulsen et al., 2014, Biofouling 30(4):513-23.
Stewart, 2011, Appl Microbiol Biotechnol 89(1):27-33.
Stewart et al., 2011, Adv Colloid Interface Sci 167(1-2):85-93.
Hennebert et al., 2015, Interface Focus 5(1):2014.
Y. Modis, S. Ogata, D. Clements, S. C. Harrison, Nature 2004, 427, 313-319.
C. D. Blanchette, Y. H. Woo, C. Thomas, N. Shen, T. A. Sulchek, A. L. Hiddessen, PLoS One 2009, 4, e6056.
J. Han, K. Burgess, Chem. Rev. 2010, 110, 2709-2728.
J. Kalia, R. T. Raines, Angew. Chem. Int. Ed. Engl. 2008, 47, 7523-7526.
J. Kalia, R. T. Raines, Angew. Chem. 2008, 120, 7633-7636.
J. Z. Du, X. J. Du, C. Q. Mao, J. Wang, J. Am. Chem. Soc. 2011, 133, 17560-17563.
E. H. Cordes, H. G. Bull, Chem. Rev. 1974, 74, 581-603.
A. Luong, T. Issarapanichkit, S. D. Kong, R. Fonga, J. Yang, Org. Biomol. Chem. 2010, 8, 5105-5109.
Fanghänel, R. Hänsel, W. Ortmann, J. Hohlfeld, J. Prakt. Chem. 1975, 317, 631-640.

(Continued)

*Primary Examiner* — Robert Havlin
(74) *Attorney, Agent, or Firm* — Nguyen & Tarbet Law Firm

(57) ABSTRACT

Water-soluble triazabutadiene molecules and methods for producing and using such compounds. The triazabutadiene molecules may be more labile at pH levels below physiological pH, such as pH 7, pH 6, pH 5, etc. The triazabutadiene molecules and compounds may be used for depositing diazonium salt and/or cargo in a pH-sensitive manner. The triazabutadiene molecules may alternatively be cleaved in reducing conditions or as a light-catalyzed reaction. The compounds herein may be used for delivery of drugs, as part of detection systems, or for other applications such as underwater adhesive applications.

13 Claims, 20 Drawing Sheets

(56) References Cited

U.S. PATENT DOCUMENTS

| | | |
|---|---|---|
| 2007/0098807 A1 | 5/2007 | Babich et al. |
| 2007/0104719 A1 | 5/2007 | Carter et al. |
| 2009/0048222 A1 | 2/2009 | Bell et al. |
| 2009/0286308 A1 | 11/2009 | Berthelot et al. |
| 2011/0245287 A1 | 10/2011 | Holaday et al. |

FOREIGN PATENT DOCUMENTS

| | | |
|---|---|---|
| WO | WO 2008/090554 A2 | 7/2008 |
| WO | WO 2009/137916 A1 | 11/2009 |
| WO | WO2015073746 A2 | 5/2015 |
| WO | WO 2015/191735 A1 | 12/2015 |

OTHER PUBLICATIONS

H.-T. Dorsch, H. Hoffmann, R. Hansel, G. Rasch, E. Fanghänel, J. Prakt. Chem. 1976, 318, 671-680.

E. Fanghänel, R. Hänsel, J. Hohlfeld, J. Prakt. Chem. 1977, 319, 485-493.

E. Fanghänel, H. Poleschner, R. Radeglia, R. Hänsel, J. Prakt. Chem. 1977, 319, 813-826.

E. Fanghänel, J. Hohlfeld, J. Prakt. Chem. 1981, 323, 253-261.

R. Radeglia, R. Wolff, T. Steiger, S. Simova, E. Fanghanel, J. Prakt. Chem. 1984, 5, 511-514.

E. Fanghänel, W. Ortmann, A. Hennig, J. Prakt. Chem. 1988, 330, 27-34.

E. Fanghänel, W. Ortmann, J. Prakt. Chem. 1989, 331, 721-725.

E. Fanghänel, J. U. Bauroth, H. Hentschel, F. Gußmann, H. Alzyadi, W. Ortmann, J. Prakt. Chem. 1992, 334, 241-247.

D. M. Khramov, C. W. Bielawski, Chem. Commun. 2005, 4958-4960.

S. Dahmen, S. Brase, Org. Lett. 2000, 2, 3563-3565.

S. Brase, Acc. Chem. Res. 2004, 37, 805-816.

D. Jishkariani, C. D. Hall, A. Demircan, B. J. Tomlin, P. J. Steel, A. R. Katritzky, J. Org. Chem. 2013, 78, 3349-3354.

D. M. Khramov, C. W. Bielawski, J. Org. Chem. 2007, 72, 9407-9417.

A. G. Tennyson, E. J. Moorhead, B. L. Madison, J. A. V. Er, V. M. Lynch, C. W. Bielawski, Eur. J. Org. Chem. 2010, 6277-6282.

W. Herrmann, C. Köcher, Angew. Chem. Int. Ed. 1997, 36, 2162-2187.

W. Herrmann, C. Köcher, Angew. Chem. 1997, 109, 2256-2282.

N. Marion, S. Díez-González, S. P. Nolan, Angew. Chem. Int. Ed. Engl. 2007, 46, 2988-3000.

N. Marion, S. Díez-González, S. P. Nolan, Angew. Chem. 2007, 119, 3046-3058.

A. F. Hegarty, In the Chemistry of Diazonium and Diazo Groups, vol. 2 (Ed: S. Patai), John Wiley & Sons, Ltd., New York, NY, 1978, pp, 511-591.

L. P. Hammett, J. Am. Chem. Soc. 1937, 59, 96-103.

B. M. Tracey, D. E. G. Shuker, Chem. Res. Toxicol. 1997, 10, 1378-1386.

J. M. Hooker, E. W. Kovacs, M. B. Francis, J. AM. Chem. Soc. 2004, 126, 3718-3719.

J. Gavrilyuk, H. Ban, M. Nagano, W. Hakamata, C. F. Barbas III, Bioconjugate Chem. 2012, 23, 2321-2328.

L. Wang, V. Gruzdys, N. Pang, F. Meng, X.-L. Sun, RSC Adv. 2014, 4, 39446.

European Journal of Inorganic Chemistry vol. 2013, Issue 12, p. 2020-2030, Apr. 2013 Elena García-Moreno, Elena Cerrada, M. José Bolsa, Asunción Luquin and Mariano Laguna.

European Journal of Medicinal Chemistry vol. 46, Issue 7, Jul. 2012, p. 2748-2758, Marijana Hranjeca, Borka Lučića, Ivana Ratkajb, Sandra Kraljević Pavelićb, Ivo Piantanidac, Krešimir Pavelićb, Grace Karminski-Zamola.

Flora Kimani and John Jewett, DOI: 10.1002/anie.201411277 Water-Soluble Triazabutadienes that Release Diazonium Species upon Protonation under Physiologically Relevant Conditions.

Chao Zhong, Thomas Gurry, Allen A. Cheng, Jordan Downey, Zhengtao Deng, Collin M. Stultz, Timothy K. Lu, Nature Nanotechnology 9, 858-866 (2014).

Stewart RJ, Ransom TC, Hlady VJ, Polym Sci B Polym Phys. Jun. 2011;49(11):757-771.

Poulsen N, Kröger N, Harrington MJ, Brunner E, Paasch S, Buhmann MT, Biofouling. 2014;30(4):513-23.

Stewart RJ, Appl Microbiol Biotechnol. Jan. 2011;89(1):27-33.

Stewart RJ, Wang CS, Shao H, Adv Colloid Interface Sci. Sep. 14, 2011;167(1-2):85-93.

Hennebert E, Maldonado B, Ladurner P, Flammang P, Santos R, Interface Focus. Feb. 6, 2015;5(1):2014.

Phosphate-buffered saline (PBS) CSH Protocols. "http://cshprotocols.cshlp.org/content/2006/1/pdb.rec8247".

Cornaii, 'Development of Clickable Triazabutadienes as Cleavable Cross—linkers', A thesis submitted to the Faculty of the Department of Chemistry and Biochemistry In Partial Fulfillment of the Requirements for the Degree of Master of Science, The University of Arizona, Apr. 8, 2016.

*Figure 6F*
*Figure 6G*
*Figure 6H*
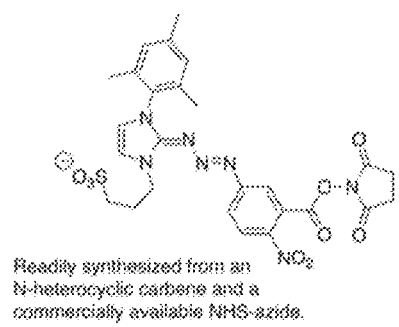
Readily synthesized from an
N-heterocyclic carbene and a
commercially available NHS-azide.
*Figure 6I*
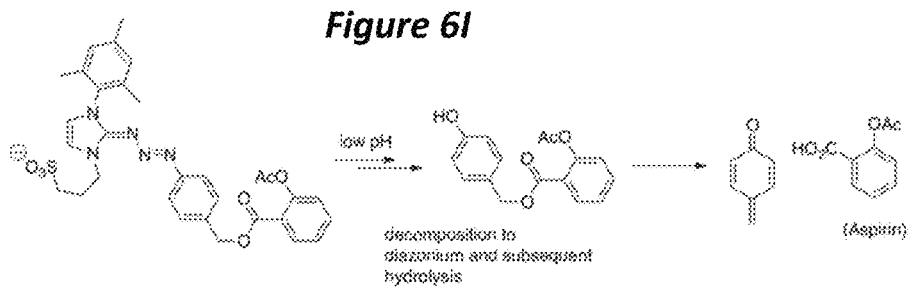
*Figure 6J*
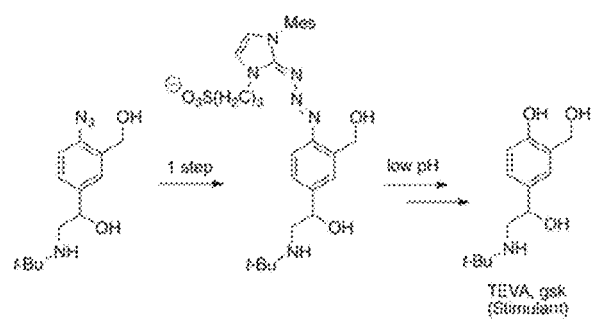

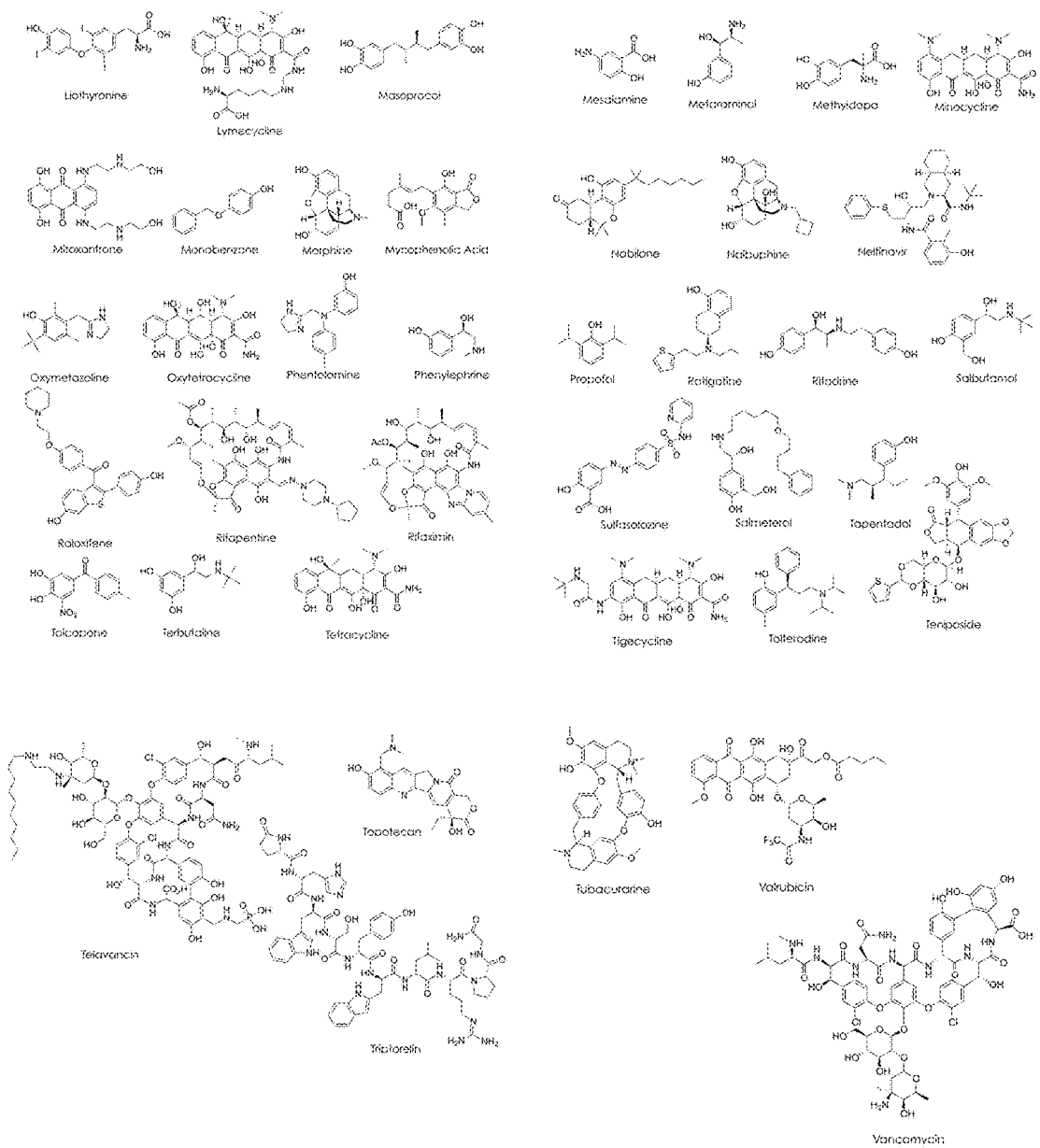
Figure 10C, cont.

WATER-SOLUBLE TRIAZABUTADIENES

This application claims priority to U.S. Provisional Application No. 62/010,861, filed Jun. 11, 2014, U.S. Provisional Application No. 62/109,170 filed Jan. 29, 2015, U.S. Provisional Application No. 62/114,735 filed Feb. 11, 2015, and U.S. Provisional Application No. 62/128,707 filed Mar. 5, 2015, the specifications of which are incorporated herein in their entirety by reference.

BACKGROUND OF THE INVENTION

The present invention also features water-soluble triazabutadiene molecules. The present invention also features methods of use (applications) of said water-soluble triazabutadiene molecules, methods of cleavage of said water-soluble triazabutadiene molecules (e.g., decomposition in water, reductive cleavage, pH-dependent cleavage, light-catalyzed cleavage, etc.), and methods of synthesis of said water-soluble triazabutadienes.

The triazabutadiene molecules of the present invention (and/or the products of triazabutadiene molecule cleavage (e.g., diazonium species) may be used for a variety of applications. For example, the triazabutadiene molecules of the present invention may be used in drug delivery systems, detection systems (e.g., cancer detection systems), probe systems, protein-protein interaction studies, and the like. For example, the triazabutadiene molecules (and/or reaction products of triazabutadiene molecules) of the present invention may be used for underwater adhesive applications.

SUMMARY

The present invention features water-soluble triazabutadiene molecules. The triazabutadiene molecules of the present invention may have a formula according to Formula 1, Formula II, Formula III, or Formula IV (see below). In some embodiments, $X^1$ comprises a moiety conferring water solubility; $Y^1$ comprises a tri-substituted aryl group; and $Z^1$ comprises an optionally substituted aryl group. In some embodiments, the tri-substituted aryl group of $Y^1$ comprises a NHS-ester moiety; an oligonucleotide; a peptide; a fluorescence quencher; a pro-fluorophore; an alkyne; a triazene; or a combination thereof; and the optionally substituted aryl of $Z^1$ comprises a NHS-ester moiety; an oligonucleotide; a peptide; a fluorescence quencher; a pro-fluorophore; an alkyne; a triazene; a biologically active acid labile compound; a prodrug comprising a phenolic functional group; an aldehyde; an amine; an aminooxy; a halogen; or a combination thereof. In some embodiments, the $X^1$ comprises a moiety of the formula —$R^1$-$Q^1$, wherein $R^1$ comprises $C_{1-6}$ alkylene, and $Q^1$ comprises sulfate, phosphate, or a quaternary ammonium cation.

In some embodiments, the triazabutadiene molecule is adapted to undergo an irreversible reaction yielding a diazonium species and a cyclic guanidine species. The reaction occurs at a reaction rate. In some embodiments, the reaction rate is increased when the triazabutadiene molecule is subjected to a lowered pH. In some embodiments, the reaction rate is increased when the triazabutadiene molecule is subjected to light (e.g., wavelength from 340 to 420 nm).

The diazonium species derived from the triazabutadiene molecule is adapted to react with an electron rich aromatic that can undergo diazonium chemistry to produce a product species. In some embodiments, the electron rich aromatic comprises a resorcinol species or a phenol species. In some embodiments, the phenol species is that of a tyrosine molecule. In some embodiments, the product species (e.g., from reaction of a diazonium species and an electron rich aromatic, e.g., phenol species) comprises an aryl azo dye (e.g., Sudan Orange).

In some embodiments, the triazabutadiene molecule is adapted to undergo an irreversible reaction in reducing conditions yielding an aniline and a hydrazine, or a urea functionality and a terminal aryl triazene. A non-limiting example of a reducing agent is sodium dithionite. In some embodiments, cleavage of the molecule by the reducing agent can be observed by a color change. In some embodiments, the triazabutadiene molecule is conjugated to a protein (e.g., antibody or any other appropriate protein). In some embodiments, the triazabutadiene molecule is conjugated to a surface, e.g., glass, plastic, the like, or a combination thereof.

In some embodiments, the triazabutadiene molecule has half-life of at least 12 hours in a pH 7.4 buffer. In some embodiments, the triazabutadiene molecule has half-life of at least 24 hours in a pH 7.4 buffer. In some embodiments, the triazabutadiene molecule has half-life of at least 36 hours in a pH 7.4 buffer.

The present invention also features methods of increasing a reaction rate of decomposition of a water-soluble triazabutadiene molecule of the present invention to a diazonium species and a cyclic guanidine species. In some embodiments, the method comprises subjecting the molecule to a lowered pH, wherein the lowered pH increases the reaction rate. In some embodiments, the method comprises subjecting the molecule to light (e.g., having a wavelength from 350 to 420 nm), wherein light increases the reaction rate. In some embodiments, the method comprises subjecting the molecule to a lowered pH and light.

The present invention also features methods of increasing a reaction rate of breakdown of a water-soluble triazabutadiene molecule of the present invention to an aniline species and a hydrazine species or a urea functionality and a terminal aryl triazene. In some embodiments, the method comprises subjecting the molecule to a reducing agent (e.g., sodium dithionite), wherein the reducing agent increases the reaction rate.

The present invention also features methods of detecting protein-protein proximity or protein-protein interactions in a sample. In some embodiments, the method comprises introducing a first protein to the sample, wherein the first protein is conjugated with a triazabutadiene molecule according to the present invention. In some embodiments, when the triazabutadiene molecule encounters a low pH in the sample, the triazabutadiene molecule undergoes an irreversible reaction yielding a diazonium species and a cyclic guanidine species. In some embodiments, an acid is introduced to the sample, and the acid lowers the pH of the sample. When the triazabutadiene molecule encounters the low pH in the sample, the triazabutadiene molecule undergoes an irreversible reaction yielding a diazonium species and a cyclic guanidine species. The diazonium species is adapted to react with a phenol group of a nearby tyrosine residue of a second protein yielding an azo dye that is visually distinct from the triazabutadiene molecule and the diazonium species. Detection of the azo dye may be indicative of proximity or interaction of the first protein and the second protein.

The present invention also features methods of detecting an environment having a low pH. In some embodiments, the method comprises introducing a molecule according to the present invention to a sample, wherein an environment having a low pH causes the triazabutadiene molecule to break down into a diazonium species and a cyclic guanidine species. The diazonium species is visually distinct from the triazabutadiene, thus visualization of the diazonium species is indicative of the low pH environment. In some embodiments, the method further comprises introducing an electron rich aromatic that can undergo diazonium chemistry to the sample, wherein the electron rich aromatic reacts with the diazonium species to form an azo dye. The azo dye is visually distinct from the diazonium species and the triazabutadiene species. Thus, detection of the diazonium species and/or the azo dye is indicative of the low pH environment.

The present invention also features methods of bonding a first surface to a second surface. In some embodiments, the method comprises treating a first surface with an acid, wherein the first surface is at least partially coated with triazabutadiene molecules according to the present invention. The acid yields a diazonium species from the triazabutadiene molecules. The method may further comprise contacting the first surface to a second surface in aqueous conditions, wherein the second surface is at least partially coated with an electron rich aromatic that can undergo diazonium chemistry. A covalent bond may be formed between the diazonium species and the electron rich aromatic so as to bond the first surface to the second surface. In some embodiments, the first surface and/or the second surface comprise glass, plastic, the like, or a combination thereof.

The present invention also features methods of releasing a cargo compound conjugated to a triazabutadiene molecule according to the present invention. In some embodiments, the method comprises subjecting the conjugate to a reducing agent or a low pH, wherein the reducing agent or the low pH initiates breakdown of the triazabutadiene molecule so as to release the cargo compound.

The present invention also features methods for delivering a drug comprising a phenolic function group to a subject in need of such a drug administration. The method may comprise administering a prodrug to the subject in need, wherein said prodrug comprises the drug comprising a phenolic functional group conjugated to a triazabutadiene molecule of the present invention. In some embodiments, the diazonium species of the triazabutadiene molecule is part of the drug. In some embodiments, the drug is formed when a diazonium species reacts to a phenol species.

The present invention also features methods for converting a drug comprising a phenolic-function group to an acid labile prodrug. The method may comprise converting the phenolic-functional group to an azide group, and reacting the azide group with an N-heterocyclic carbene compound functional group to produce an acid labile prodrug comprising a triazylidene moiety. In some embodiments, the drug is an anti-cancer drug.

The present invention also features an adhesive system. In some embodiments, the adhesive system comprises a first surface (e.g., glass, plastic, the like, or a combination thereof), wherein the first surface is at least partially coated with a triazabutadiene molecule according to the present invention or a diazonium species derived from said triazabutadiene molecule; and a second surface (e.g., glass, plastic, the like, or a combination thereof), wherein the second surface is at least partially coated with an electron rich aromatic that can undergo diazonium chemistry. When the first surface is contacted with the second surface in aqueous conditions, a covalent bond may be formed between the diazonium species and the electron rich aromatic so as to bond the first surface to the second surface.

The present invention also features an adhesive kit. In some embodiments, the adhesive kit comprises a first surface (e.g., glass, plastic, the like, or a combination thereof), wherein the first surface is at least partially coated with a triazabutadiene molecule according to the present invention or a diazonium species derived from said triazabutadiene molecule; and a second surface (e.g., glass, plastic, the like, or a combination thereof), wherein the second surface is at least partially coated with an electron rich aromatic that can undergo diazonium chemistry. The first surface and the second surface are adapted to bond together when subjected to aqueous conditions. In some embodiments, the kit further comprises an acid for treating the triazabutadiene molecule on the first surface so as to yield a diazonium species on the first surface.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIGS. 6A, 6B, 6C, 6D, 6E, 6F, 6G, 6H, 6I, and 6J show non-limiting examples of triazabutadienes.

DESCRIPTION OF PREFERRED EMBODIMENTS

I. Triazabutadiene Molecules

The present invention features water-soluble triazabutadiene molecules. Examples of formulas for triazabutadiene molecules of the present invention are of shown in FIG. 1. The present invention is not limited to Formula I, Formula II, Formula III, and Formula IV.

Figure 1:
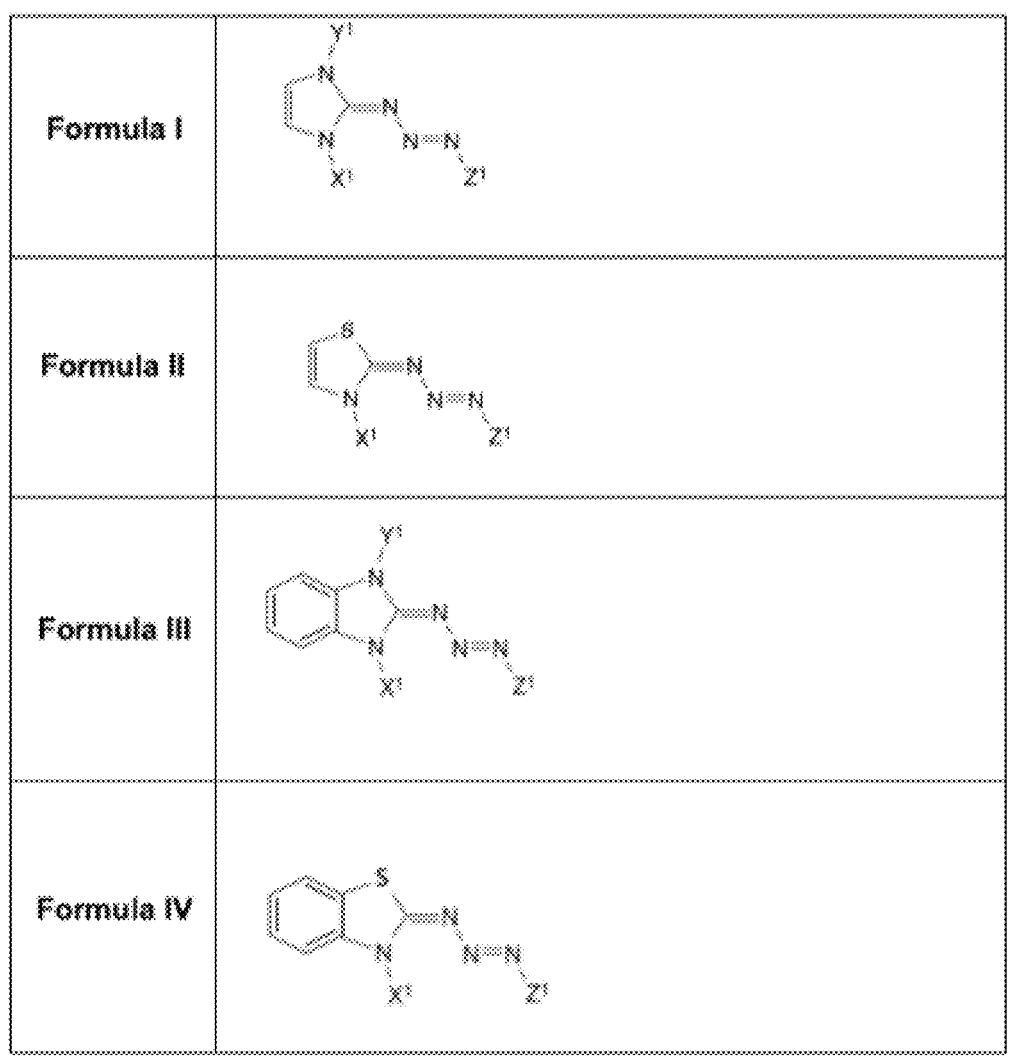
FIG. 1 shows examples of formulas of water-soluble triazabutadiene molecules of the present invention.

Referring to FIG. 1, in some embodiments, $X^1$ is a moiety conferring water solubility. In some embodiments, $Y^1$ is a tri-substituted aryl group. In some embodiments, the $Y^1$ (e.g., the tri-substituted aryl group) comprises a NHS-ester moiety (e.g., for protein linkage); an oligonucleotide; a peptide; a fluorescence quencher; a pro-fluorophore; an alkyne (e.g., for click chemistry); a triazene (e.g., from click reaction); the like, or a combination thereof. In some embodiments, $Y^1$ comprises an aldehyde; an amine (e.g., Fmoc protected), aminooxy, halogen (e.g., radio isotope); the like, or a combination thereof. In some embodiments, $Z^1$ is an optionally substituted aryl. In some embodiments, $Z^1$ comprises a NHS-ester moiety; an oligonucleotide; a peptide; a fluorescence quencher; a pro-fluorophore; a biologically active acid labile compound; a prodrug comprising a phenolic functional group; releasable cargo; an alkyne (e.g., for click chemistry); a triazene (e.g., from click reaction); the like, or a combination thereof. In some embodiments, $Z^1$ comprises an aldehyde; an amine (e.g., Fmoc protected), aminooxy, halogen (e.g., radio isotope); the like, or a combination thereof.

As previously discussed, $X^1$ may comprise a functional group that confers water solubility. In some embodiments, $X^1$ comprise a moiety of the formula $—R^1-Q^1$, wherein $R^1$ is $C_{1-6}$ alkylene, and $Q^1$ is sulfate, phosphate, or a quaternary ammonium cation. In some embodiments, $X^1$ is a moiety of the formula $—R^1-Q^1$, wherein $R^1$ is $C_{1-6}$ alkylene, and $Q^1$ is sulfate (e.g., $—(O)_nSO_3R^a$, where n is 0 or 1, and $R^a$ is C1-6 alkyl or typically H), phosphate (e.g., $—(O)_nPO_3R^a$, where n is 0 or 1, and $R^a$ is C1-6 alkyl or typically H), or a quaternary ammonium cation (e.g., $—[NR^aR^bR^c]^+$, where each of $R^a$, $R^b$, and $R^c$ is independently H or $C_{1-6}$ alkyl). As used herein, the term "alkyl" refers to a saturated linear monovalent hydrocarbon moiety of one to twelve, typically one to six, carbon atoms or a saturated branched monovalent hydrocarbon moiety of three to twelve, typically three to six, carbon atoms. Examples of alkyl groups include, but are not limited to, methyl, ethyl, n-propyl, 2-propyl, tert-butyl, pentyl, and the like. The term "alkylene" refers to a saturated linear divalent hydrocarbon moiety of one to twelve, typically one to six, carbon atoms or a branched saturated divalent hydrocarbon moiety of three to twelve, typically three to six, carbon atoms. Examples of alkylene groups include, but are not limited to, methylene, ethylene, propylene, butylene, pentylene, and the like.

In general, the triazabutadiene molecules of the present invention are readily soluble in water. In some embodiments, the solubility of the triazabutadiene molecules of the present invention in water is at least 23 g/L of water (50 mM). In some embodiments, the triazabutadiene molecules of the present invention are stable in pH 7.4 phosphate buffer. The phosphate buffer solutions are commercially available or can be prepared, for example, as described in http://cshprotocols.cshlp.org/content2006/1/pdb.rec8247. In some instances, the half-life of the triazabutadiene molecules of the present invention in pH 7.4 phosphate buffer solution is at least 24 hours.

Stability of the triazabutadiene molecule can be measured in various ways. In some embodiments, stability is measured by the half-life of the molecule. In some embodiments, the molecule has a half-life of at least 12 hours in a pH 7.4 buffer. In some embodiments, the molecule has half-life of at least 24 hours in a pH 7.4 buffer. In some embodiments, the molecule has half-life of at least 36 hours in a pH 7.4 buffer. The present invention is not limited to the aforementioned examples of stability measurements.

Without wishing to limit the present invention to any theory or mechanism, it is believed that the triazabutadiene molecules of the present invention are advantageous because the triazabutadiene molecules can be easily modified (e.g., various different functional groups can be easily used as $X^1$, $Y^1$, or $Z^1$ (see FIG. 1). And, the release of the diazonium species following triazabutadiene molecule breakdown (via certain mechanisms, as described below) may provide a new functional group that can be taken advantage of in various applications. Also, it may be considered advantageous that the breakdown of the triazabutadiene molecule is irreversible.

II. Cleavage of Triazabutadiene Molecules a. Water and/or Low pH

Figure 2A:
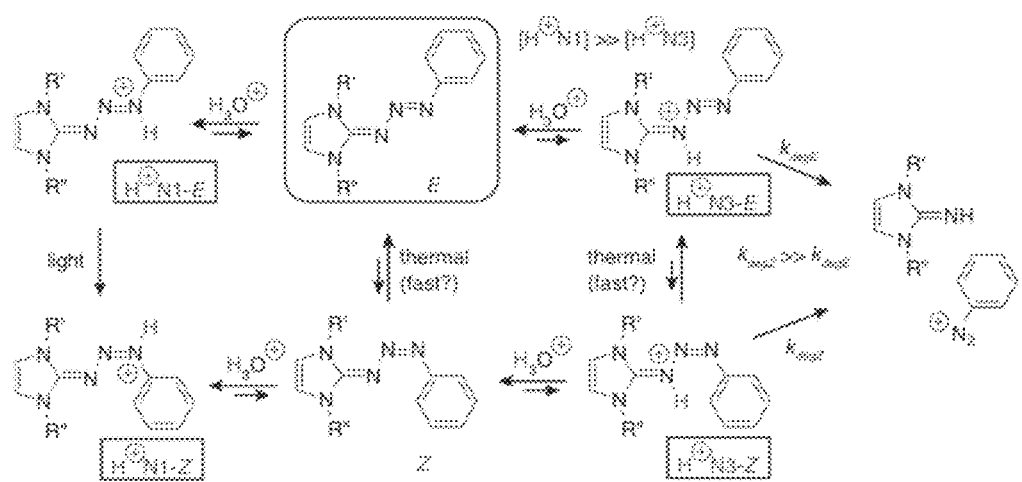
FIG. 2A shows triazabutadiene molecules undergoing decomposition to diazonium salts (and cyclic guanidine species). Note the Reaction/equilibrium arrows are not to scale.

The present invention shows that triazabutadiene molecules may break down in the presence of water to generate reactive aryl diazonium compounds. For example, FIG. 2A shows that triazabutadiene molecules of the present invention can undergo decomposition to diazonium salts (reactive aryl diazonium compounds) and cyclic guanidine species. Aryl diazonium compounds can react with electron-rich aryl rings (e.g., aryl species wherein the bond of interest is a nitrogen-carbon bond; indoles, anilines, phenol-containing compounds such as resorcinol or tyrosine, etc.) to form stable azobenzene linkages (e.g., an aryl azo dye, e.g., Sudan Orange) (e.g., see FIG. 5, top scheme). The phenol-containing species is not limited to the aforementioned examples. In some embodiments, imidazole compounds (e.g., purine bases like guanine) may be used in lieu of a phenol-containing compound.

Figure 5:
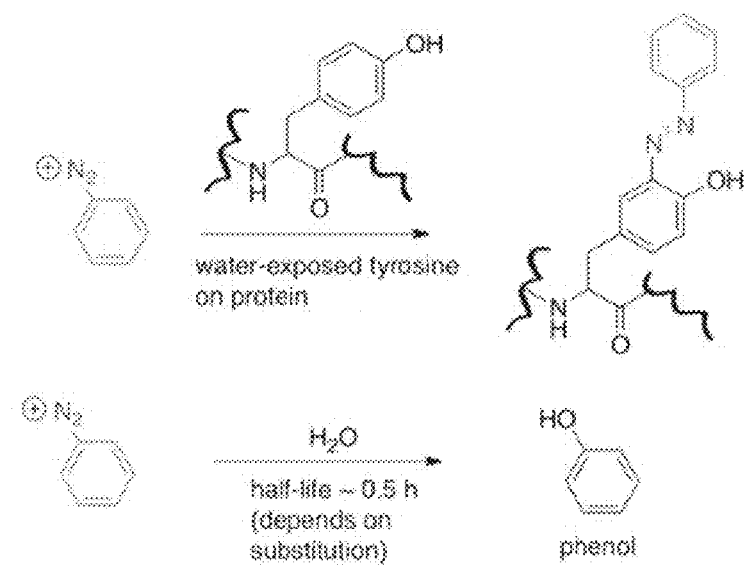
FIG. 5 shows reactions with aryl diazonium species in water. In the top scheme, the phenol-containing species is a tyrosine molecule (on a protein). In the bottom scheme, the diazonium species decomposes into a phenol species.

Referring to FIG. 5 (bottom scheme), the diazonium species may not necessarily react with an electron-rich aryl rings compound (e.g., phenol species), for example if a phenol species is not present. The diazonium species may irreversibly extrude nitrogen gas to generate an aryl cation, which will rapidly be quenched by solvating water, thus synthesizing a new phenolic compound (e.g., HO-Ph, wherein Ph refers to the phenyl ring); thus, the diazonium portion of the triazabutadiene molecule may function as a masked hydroxyl group.

In some embodiments, the triazabutadiene molecules are acid labile (e.g., unstable at particular pH levels). For example, decreases in pH increase the rate at which the triazabutadiene molecules break down (the half life of the molecule decreases). In some embodiments, the triazabutadiene molecules are unstable at low (lowered) pH levels (e.g., lowered pH as compared to a particular pH that the molecule may be stored at, e.g., a pH wherein the molecule has a particular desired half life). Low pH levels, in some example, may be a sub-physiological pH (7.4 or less). In some embodiments, the triazabutadiene molecules are (more) unstable at pH 7.0 or less, pH 6.8 or less, pH 6.5 or less, pH 6.2 or less, pH 6.0 or less, pH 5.8 or less, pH 5.6 or less, pH 5.5 or less, pH 5.2 or less, pH 5.0 or less, etc. In some embodiments, the triazabutadiene molecule has a half-life of at least 8 hours. In some embodiments, the triazabutadiene molecule has a half-life of at least 10 hours. In some embodiments, the triazabutadiene molecule has a half-life of at least 12 hours. In some embodiments, the triazabutadiene molecule has a half-life of at least 20 hours. In some embodiments, the triazabutadiene molecule has a half-life of at least 24 hours. In some embodiments, the triazabutadiene molecule has a half-life of at least 30 hours. In some embodiments, the triazabutadiene molecule has a half-life of at least 36 hours.

The term 'low pH" may refer to several different pH levels. Since the functional groups attached to the molecule (e.g., see $X^1$, $Y^1$, $Z^1$ of Formula I) affect the stability of the molecule (as well as water solubility), the pH that is necessary to increase the rate of breakdown of the triazabutadiene molecule (e.g., the "lowered pH") may be different for different molecules. In some embodiments, the low pH is a pH of 7.4 or less. In some embodiments, the low pH is a pH of 7.2 or less. In some embodiments, the low pH is a pH of 7.0 or less. In some embodiments, the low pH is a pH of 6.8 or less. In some embodiments, the low pH is a pH of 6.6 or less. In some embodiments, the low pH is a pH of 6.6 or less. In some embodiments, the low pH is a pH of 6.6 or less. In some embodiments, the low pH is a pH of 6.5 or less. In some embodiments, the low pH is a pH of 6.4 or less. In some embodiments, the low pH is a pH of 6.2 or less. In some embodiments, the low pH is a pH of 6.0 or less. In some embodiments, the low pH is a pH of 5.8 or less. In some embodiments, the low pH is a pH of 5.5 or less. In some embodiments, the low pH is a pH of 5.0 or less.

In some embodiments, the triazabutadiene molecules can break down without the presence of the low pH (the molecules have half lives); however, in some embodiments, a lowered pH enhances the reaction (e.g., increases the rate of reaction). As such, a low pH may or may not be used with the molecules and/or methods of the present invention.

The present invention also features methods of breaking down triazabutadiene molecules. In some embodiments, the method comprises subjecting the molecule to water. In some embodiments, the method comprises subjecting the molecule to a low pH (e.g., a low pH that is appropriate for the molecule, e.g., a lowered pH that increases the rate at which the triazabutadiene molecule breaks down).

In some embodiments, the diazonium species may be visually differentiated from the triazabutadiene species, e.g., the diazonium species is visually distinct (e.g., a different color) from the triazabutadiene molecule. If applicable, in some embodiments, the aryl azo dye may be visually differentiated from the triazabutadiene species and the diazonium species, e.g., the aryl azo dye is visually distinct (e.g., a different color) from the triazabutadiene species and the diazonium species.

Given the possibility that the aryl azo dye is visually distinct from the triazabutadiene molecule (and/or the diazonium species), the present invention also features methods of producing a visually detectable molecule. In some embodiments, the method comprises providing a triazabutadiene molecule according to the present invention and subjecting the triazabutadiene molecule to water and/or a low pH (or light as discussed below, or light and low pH, etc.). The low pH (or light, or light and low pH, etc.) initiates (e.g., increases the rate of) the irreversible reaction to produce the diazonium species and the cyclic guanidine species. As previously discussed, the diazonium species may be visually distinct from the triazabutadiene molecule; therefore the reaction produces a visually detectable molecule.

b. Reductive Cleavage

Other mechanisms may be used to break down triazabutadiene molecules of the present invention. For example, in some embodiments, reducing conditions increase the rate at which the triazabutadiene molecules break down. Thus, the present invention also features methods of reductive cleavage of triazabutadiene molecules. For example, triazabutadiene molecules (e.g., triazabutadiene scaffolds) may be readily cleaved using reducing agents such as but not limited to sodium dithionite (sodium hydrosulfite) ($Na_2S_2O_4$). In some embodiments, the reducing agent comprises lithium aluminum hydride, sodium borohydride, or the like. In some embodiments, electrochemical reduction may be used in accordance with the present invention.

Figure 3:
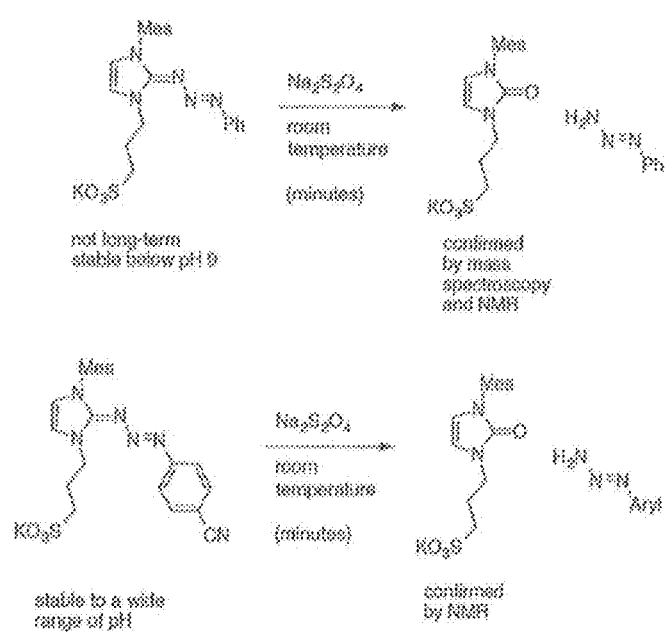
FIG. 3 shows reductive cleavage of triazabutadiene molecules.

Reductive cleavage of the triazabutadiene molecules provides a urea functionality and a terminal aryl triazene (see FIG. 3). In some embodiments, the aryl triazene is further reduced in the presence of excess reducing agent (e.g., sodium dithionite). In some embodiments, the reduction can be observed visually by the change in color of a solution. For example, there may be a subtle change of yellows that results from a loss of a shoulder in UV/vis spectrum.

In some embodiments, the ratio of the concentration of the triazabutadiene to the reducing agent is about 1:1. In some embodiments, the ratio of the concentration of the triazabutadiene to the reducing agent is about 1:2. The present invention is not limited to the aforementioned ratios. For example, in some embodiments, the ratio of the concentration of the triazabutadiene to the reducing agent is about 2:3, 4:5, etc. The present invention is not limited to the aforementioned ratio of concentrations.

In some embodiments, the reduction can occur within about 10 minutes, within about 15 minutes, within about 20 minutes, within about 25 min, within about 30 min, etc., at room temperature.

Without wishing to limit the present invention to any theory or mechanism, it is believed that reductive cleavage of the triazabutadiene molecules is advantageous because it can occur rapidly (e.g., within 10 minutes, within 15 minutes). Also, the triazabutadiene molecules that are highly stable in acid (e.g., a p-CN derived triazabutadiene) may still be susceptible to reducing conditions.

c. Light-Initiated Cleavage

Figure 4A:
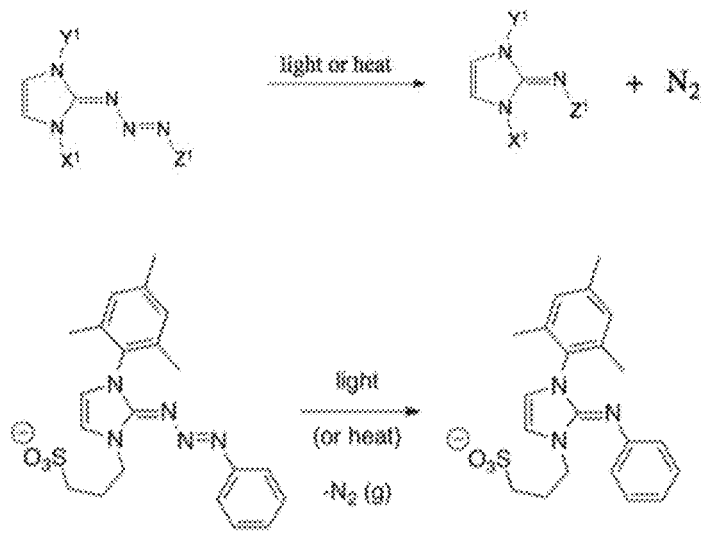
FIG. 4A shows light catalyzed cleavage of triazabutadiene molecules.

Other factors (e.g., in addition to low pH, in addition to reducing conditions) may also enhance or increase the rate of the breakdown of the triazabutadiene molecules. For example, in some embodiments, light increases the rate at which the triazabutadiene molecule breaks down (into the cyclic guanidine species and the diazonium species) (see FIG. 4A).

Figure 4B:
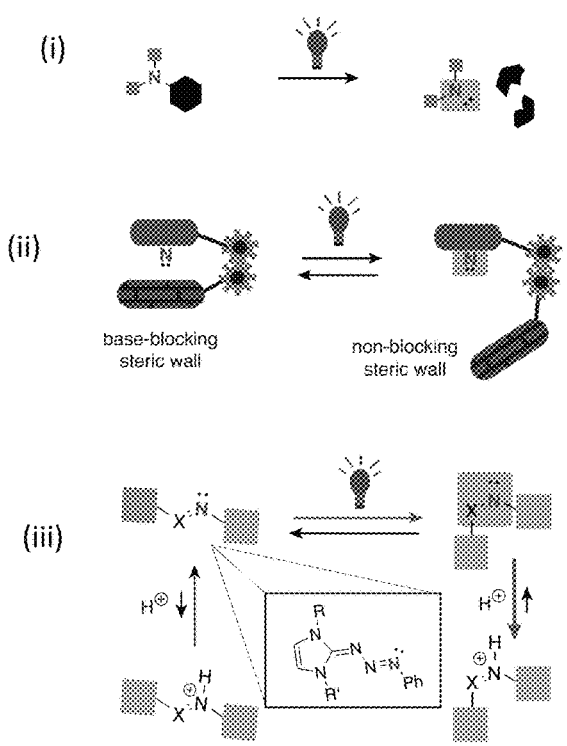
FIG. 4B shows photochemically generated bases. (i) A masked base may decompose to reveal a basic nitrogen atom upon exposure to light; (ii) The basic nitrogen atom of a molecule obscured by a steric wall may be reversibly swung away in a photochemically triggered fashion; (iii) The intrinsic basicity of a nitrogen-containing functional group may be altered by a photochemical event.

The present invention features water-soluble triazabutadienes that, upon photo-irradiation, may be rendered more basic in a reversible fashion. Referring to FIG. 4B, for reference, a protecting group of a masked base may decompose to reveal a basic nitrogen atom upon exposure to light. Or, a basic nitrogen atom of a molecule obscured by a steric wall may be reversibly swung away in a photochemically-triggered manner. The present invention shows the intrinsic basicity of a nitrogen-containing functional group may be altered by a photochemical event.

In some embodiments, triazabutadiene molecules of the present invention may readily photoisomerize to a more reactive Z-form. An aqueous solution of Compound A was irradiated with a simple hand-held UV lamp ("365 nm," measured at 350 nm). Consumption of Compound A was observed after only a few hours. The non-irradiated reaction under similar conditions was stable for days as partial degradation rapidly renders the solution mildly basic. Without wishing to limit the present invention to any theory or mechanism, it was hypothesized that if a two-electron process were happening, then Compound A-Z would be more basic than Compound A-E. A 1.0 N NaOH solution of Compound A was treated with light. At pH 14, Compound A was stable for weeks in the dark; it was surprisingly discovered that near complete consumption of starting material after 20 hours of constant irradiation occurred.

Figure 4C:
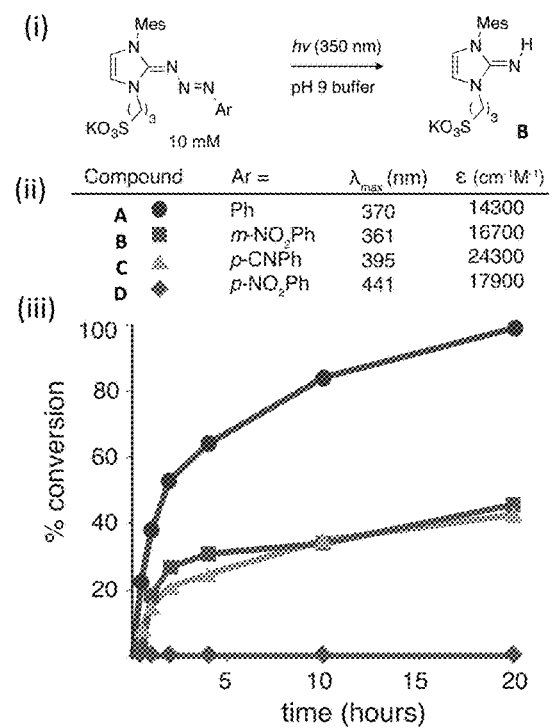
FIG. 4C shows time-dependent photo-induced degradation of triazabutadienes. (i) The reaction was monitored by comparing starting materials (Compounds A-E) with product (Compound B); (ii) Peak absorption and extinction coefficients for all of the compounds were excitable by the UV source used; (iii) Time-dependent conversion of compounds was measured by NMR integration.

Referring to FIG. 4C, NMR analysis of samples post-irradiation showed cyclic guanidine Compound B. Evidence of a benzene diazonium species or phenol/azobenzene products derived therefrom was not observed. Benzene diazonium ions also absorb UV light to expel nitrogen and generate a benzene radical. In order to resolve if the initial cleavage undergoes a radical homolytic mechanism versus a two-electron heterolytic mechanism, a trapping experiment using resorcinol was conducted. (Resorcinol was chosen because it can serve a dual role as a radical scavenger and a trap benzene diazonium species that could be formed.) An excess of resorcinol was added to a pH 9 borate-buffered solution of Compound A and the mixture was irradiated with light. The known azobenzene, Sudan Orange G, was formed in a 65% yield (versus 4% for the non-irradiated reaction).

Derivatives of Compound A were made to examine the effects of electronic perturbations on the light-induced degradation. Electron deficient aryl rings are more stable at lower pH, and this trend generally holds true for the photochemical reactions as well. A buffered borate solution was chosen due to its alkaline nature and lack of complicating signals in the NMR experiment. Compounds C-E all have absorption spectra that are well within the range of the UV lamp (see FIG. 4C(ii)). Both m-$NO_2$ (Compound C) and p-CN (Compound D) had similar rates of reaction, both slower than Compound A. To rule out other effects associated with possible heating or interactions of the buffer, p-$NO_2$ derivative Compound E was irradiated because of its significantly red-shifted spectrum. Compound E absorbed in a range that was not irradiated with the UV lamp and as such was recalcitrant to degradation (see FIG. 4C(iii)).

As previously discussed, poorly (or non-) buffered aqueous solutions could become more basic as a function of time due to the degradation to Compound B and the aryl diazonium species. Without wishing to limit the present invention to any theory or mechanism, it is believed that the cause of the increase in pH is Compound B, which acts as a base. It was found that reactions slowed and eventually stopped once the pH had risen to around 9. Without wishing to limit the present invention to any theory or mechanism, it was hypothesized that by driving the reaction to completion with light, it would be possible to increase the pH beyond this dark-reaction imposed wall (analogous FIG. 4B(ii)). Using NMR and a pH meter, it was observed that the pH of a solution of Compound A irradiated with UV light rose in a time-dependent manner.

In an effort to examine the rate order for the pH-increasing reaction more carefully, in situ, real-time pH measurements were acquired. Compound A was dissolved in water and the pH of the solution was adjusted to 9 such that it would not form Compound B in the absence of light. Upon exposing the solution to 350 nm light, it was surprisingly discovered that the solution rapidly spiked up to a pH of ~10 over the course of several minutes, and only upon much longer exposure slowly became more basic. This spike was not at all consistent with the model of the pH increase being solely linked to the concentration of Compound B being generated. Moreover, previous NMR studies showed that much more time was required to afford a pH change commensurate with this apparent level of degradation.

Figure 4D:
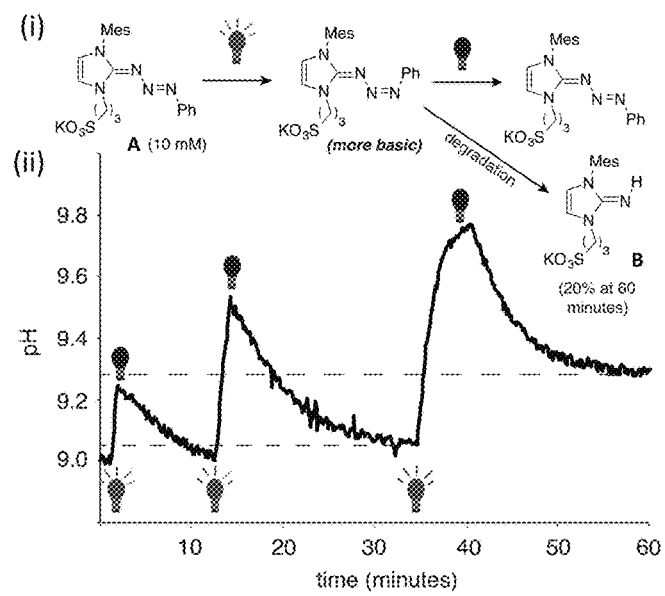
FIG. 4D shows (i) Compound A is rendered more basic upon exposure to light; that basicity recovers (to some extent) in the absence of light; (ii) Oscillating UV irradiation provides a saw-tooth pH trend over time.

Without wishing to limit the present invention to any theory or mechanism, it was hypothesized that the rapid pH increase that was observed was not attributed to Compound B, but instead a result of the Z isomer being significantly more basic than the E isomer (see FIG. 4D(i). A sample was irradiated and then the light was turned off once the pH of the solution started to increase noticeably. As the sample thermally reverted to the more stable E form, the pH of the solution dropped as well (see FIG. 4D(ii)). The experiment was repeated with increasing times of irradiation, and a saw-tooth pattern was obtained. The process was not completely reversible due to some degradation to Compound B. Indeed, triazabutadiene Compound A can serve a dual role of being a photo-masked base (see FIG. 4B(i)), and a base whose intrinsic functional group properties are altered photochemically (FIG. 4B(i)).

Figure 4E:
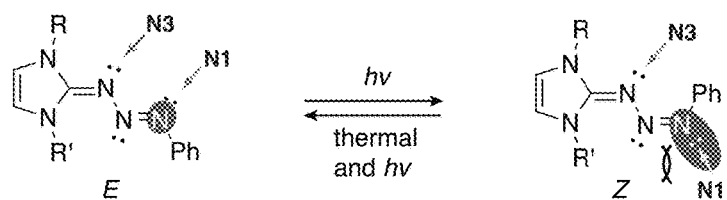
FIG. 4E shows the lone-pair of electrons on the N1 nitrogen atom becomes more electron-rich upon isomerization from E to Z.

Thus, this phenomenon via an isomerization-induced $pK_b$ change was surprisingly discovered by the inventor. Without wishing to limit the present invention to any theory or mechanism, unlike the case where Hecht's compound is rendered basic upon irradiation by way of moving of a steric wall (see FIG. 4B(ii), it is unlikely that steric factors play a significant role in this chemistry, especially in water. It is possible that the E isomer has alternating non-π involved lone pairs of electrons, whereas the Z isomer has two adjacent lone pairs of electrons (see FIG. 4E). The electronic repulsion from these renders N1 much more electron rich, and thus a stronger Lewis base.

Referring to FIG. 4C(iii), Compound C and Compound D were examined in an effort to find a base that was reversibly basic but also more resistant to degradation. In both cases, a slow subtle change to the pH was observed, but none as dramatic and rapid as Compound A. Without wishing to limit the present invention to any theory or mechanism, it is believed that this may be due to factors such as (a) faster thermal isomerization to the E isomer such that a build up of the Z isomer is not possible; (b) the electron-deficient triazabutadienes are less basic to begin with, so a transition is not observable in the operating pH range.

It is possible that Compound A may be useful as a photo-catalytic base in the context of organic reactions. With limited solubility in all but DMSO, the stability of Compound A was tested. As noted previously, Compound A is quite stable to an excess of acetic acid in DMSO, showing only 12% degradation over 14 hours at room temperature. Upon irradiation with light, Compound A in presence of acetic acid completely fell apart over the same time frame. To confirm that this was due to the acid, a solution of Compound A (in pure DMSO) was irradiated. After four hours of constant irradiation in acid-free DMSO, an E:Z ratio of nearly 50:50 was observed. Moreover, unlike in water, the thermal reversion from Z to E is slow in pure DMSO with a half-life on the order of days. Attributing this to lack of protonation, a control in MeOD was run, and a first-order thermal isomerization was observed with a rate of $3 \times 10^{-5}$ s$^{-1}$ ($t_{1/2}$~6.4 hours), in addition to some degradation to Compound B.

Figure 4F:
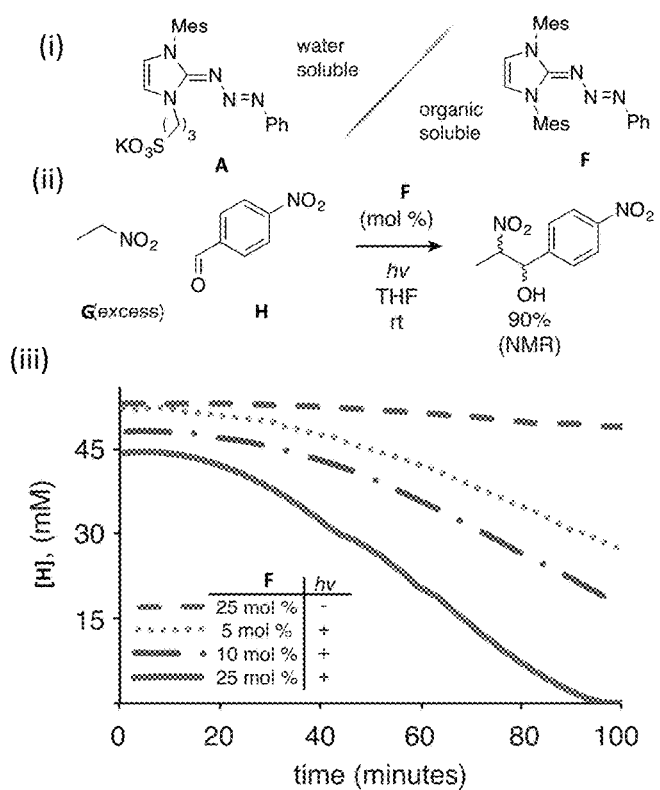
FIG. 4F shows the use of the photobase as a catalyst. (i) Structures of water-soluble Compound A versus organic soluble Compound F; (ii) The Henry reaction between Compound G and Compound H was carried out at room temperature and varying amounts of catalyst; (iii) The reactions were monitored by ReactIR™, following consumption of aldehyde Compound H. Red line=25 mol % Compound F with no light. Orange line=5 mol % Compound F+light. Green line=10 mol % Compound F+light. Blue line=25 mol % Compound F+light.

Due to the limited organic solubility of Compound A, Compound F (FIG. 4F(i)) was synthesized. With Compound F, a similar light-induced acid sensitivity was observed in DMSO (and slow thermal isomerization). Based on the apparent p$K_b$ of Compound F, p$K_a$ were matched to condensation substrates. A Henry reaction between nitroethane (Compound G) and p-nitrobenzaldehyde (H) was chosen to demonstrate the virtues of Compound F (FIG. 4F(ii)). The reaction between Compound G and Compound H occurred rapidly at room temperature in a light and catalyst dependent manner (FIG. 4F(iii)). The reaction with 25 mole % Compound F in the absence of light was exceedingly slow. Likewise, the reaction with light but no catalyst also failed to proceed. The cyclic guanidine was not observed during a post-reaction analysis of the components from a 25 mole % Compound F run, indicating that the Z-isomer of Compound F is likely to be the catalytically active species in solution. Slow thermal isomerization back to the E-isomer in aprotic organic solvents together with a fast overall reaction attempts to adjust the reaction rate prior to consumption of Compound H. Interestingly, the reaction catalyzed with Compound F was significantly faster than the same reaction reported by Hecht. This may provide evidence that Compound F-Z is more basic than Hecht's blocked trialkylamine.

As previously discussed, the present invention features methods of breaking down triazabutadiene molecules by subjecting the molecule to light. The light may, for example, include wavelengths of about 400 nm. The present invention is not limited to wavelengths of 400 nm or about 400 nm. For example, in some embodiments, the wavelength is from 350 nm to 400 nm (e.g., 370 nm). In some embodiments, the wavelength is from 360 nm to 410 nm. In some embodiments, the wavelength s from 330 nm to 420 nm. In some embodiments, the wavelength is from 340 nm to 430 nm.

In some embodiments, the method comprises subjecting the molecule to a low pH and to light.

As previously discussed, light-promoted reactivity and light-facilitating E/Z isomerization has been observed. In some embodiments, a system such as a UV-LED pen may be used for these reactions, however the present invention is not limited to a UV-LED pen and may utilize any appropriate system. The UV-LED pens may allow for relatively narrow bandwidth irradiation of these compounds (but are not limited to these bandwidths). The color of the bulk material shifts as a result of electronic perturbations to the aryl azide starting material. For example, nitro derivative Compound 6e (see FIG. 6D) is rust-red, versus an orange phenyl (Compound 6c, FIG. 6C) and yellow-orange methoxy (Compound 6d, FIG. 6D). It may be possible for selective irradiation of a complex mixture in an orthogonal sense. These experiments may be performed in basic aqueous solutions to maintain the solvation properties of water while also preventing the degradation pathway stemming from protonation. These experiments are not limited to basic aqueous solutions.

III. Synthesis of Water-Soluble Triazabutadiene Molecules and Experimental Examples Synthesis of 1-mesityl-1-H-imidazole: To a solution of 2,4,6-trimethylaniline (1.35 g, 10.0 mmol) in methanol (15 mL) was added a solution of glyoxal (40%) (1.14 mL, 40% in water, 10. mmol). The mixture was stirred at room temperature until a solid formed. Thereafter, solid ammonium chloride (1.07 g, 20 mmol), formaldehyde (37%) (1.6 mL 37% in water, 60. mmol) and methanol (40 mL) were added, and the mixture was heated to reflux for one hour. After the hour, phosphoric acid (1.4 ml of an 85% solution) was added drop wise and the mixture was refluxed for an additional eight hours. Upon cooling to room temperature ice (30 g) was added and the solution was brought to a pH of 9 with potassium hydroxide (40% in water). The following mixture was extracted repeatedly with diethyl ether. The ether phase was dried over magnesium sulfate and solvent removed in vacuo to form a brown solid which was filtered and washed with hexanes to give the product (0.785 g; 42%). 1H NMR (500 MHz, CDCl3): δ 7.45 (t, J=1.1 Hz, 1H), 7.25 (t, J=1.1 Hz, 1H), 6.99 (dp, J=1.3, 0.7 Hz, 2H), 6.91 (t, J=1.3 Hz, 1H), 2.36 (t, J=0.7 Hz, 3H), 2.01 (t, J=0.6 Hz, 6H). 13C NMR (126 MHz, CDCl3) δ 138.80, 137.47, 135.42, 133.40, 129.55, 128.96, 120.02, 21.03, 17.33. (see Liu, J. et al. Synthesis 2003, 17, 2661-2666).

Synthesis of 3-(1-mesityl-1H-imidazol-3-ium-3-yl) propane-1-sulfonate (see FIG. 6F): To a solution of 1-mesityl-1-H-imidazole (1.00 g, 5.36 mmol) in toluene (30 mL) was added 1,3-propanesultone (1.00 g, 8.18 mmol) and the mixture was heated to reflux overnight. The mixture was allowed to cool to room temperature and the off-white precipitate collected by filtration. The precipitate was further washed with diethyl ether and dried using a vacuum oven to yield a solid (1.40 g; 84%). 1H NMR (500 MHz, D2O): δ 8.92 (t, J=1.6 Hz, 1H), 7.75 (t, J=1.8 Hz, 1H), 7.49 (t, J=1.8 Hz, 1H), 7.06 (q, J=0.8 Hz, 2H), 4.44 (t, J=7.1 Hz, 2H), 2.39-2.31 (m, 2H), 2.25 (s, 3H), 1.96 (s, 6H). 13C NMR (126 MHz, D2O) δ 141.42, 136.54, 134.64, 130.74, 124.34, 123.00, 48.18, 47.17, 25.03, 20.17, 16.29.

Synthesis of Potassium 3-(3-mesityl-2-(phenyltriaz-2-en-1-ylidene)-2, 3-dihydro-1H-imidazol-1-yl) propane-1-sulfonate (see FIG. 6G): To a slurry of 3-(1-mesityl-1H-imidazol-3-ium-3-yl)propane-1-sulfonate (50 mg, 0.16 mmol) in dry THF (6 mL), was added a solution of phenyl azide in THF (0.16 mL, 1 M, 0.16 mmol). To the solution was added KO-t-Bu (24 mg, 0.21 mmol) in one portion and the resulting mixture was stirred under argon for 4 hours. Hexanes (1 mL) was then added and the reaction mixture was filtered. The solvent was removed and the residue taken up in a minimal amount of DCM and on trituration with hexanes, pure product was obtained by filtration as a yellow powder (61 mg, 81%). 1H NMR (500 MHz, DMSO-d6) δ 7.32 (d, J=2.4 Hz, 1H), 7.07-7.02 (m, 4H), 6.99-6.94 (m, 1H), 6.84 (d, J=2.4 Hz, 1H), 6.51-6.47 (m, 2H), 4.09 (t, J=7.1 Hz, 2H), 2.34 (s, 3H), 2.12-2.04 (m, 2H), 1.95 (s, 6H). 13C NMR (126 MHz, DMSO-d6) δ 152.19, 151.13, 137.94, 136.15, 134.31, 129.31, 128.60, 125.26, 120.90, 117.61, 117.24, 48.52, 45.05, 25.80, 21.06, 17.95.

Using the procedures described herein, the p-methoxy and p-nitro analogs (from the p-MeO aryl azide and p-NO2 aryl azide) were also prepared.

Figure 12:
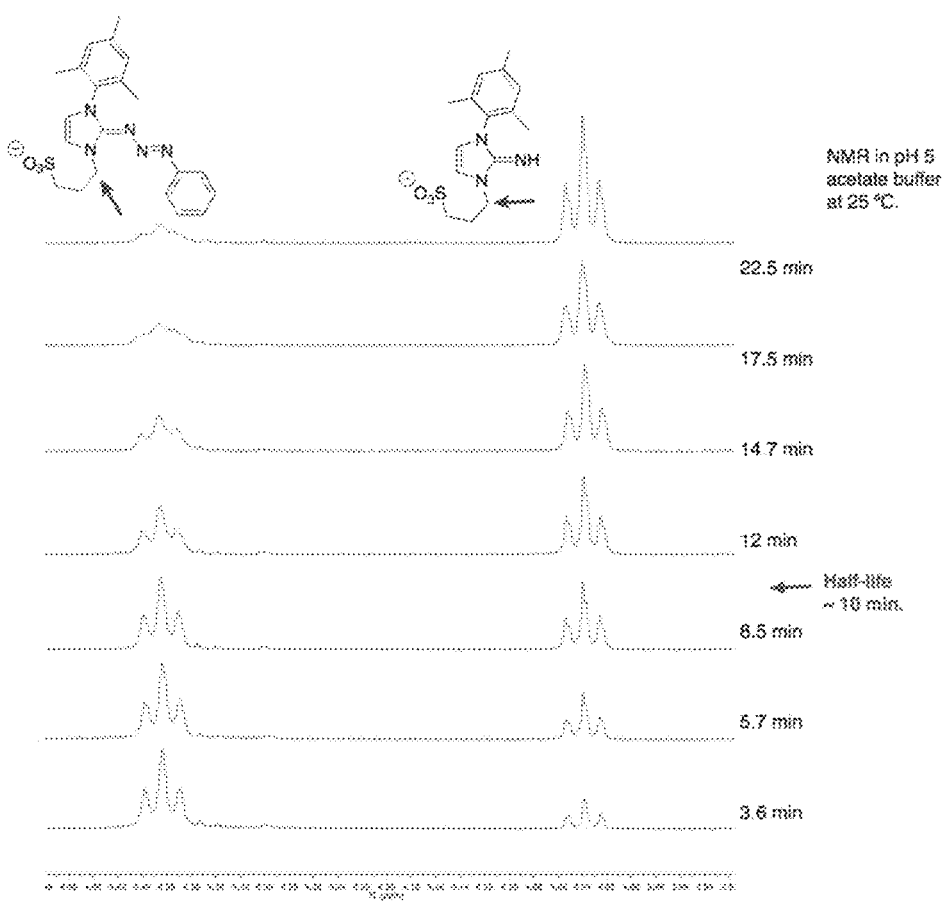
FIG. 12 shows NMR in pH 5 acetate buffer at 25 degrees C.

For decomposition experiments, buffers were made to the appropriate pH in a 9:1 mix of H2O:D2O. These solutions were added to the compound being assayed such that the buffer capacity was at least 10 fold the concentration of the compound. Some experiments used 5 mg compound in 0.5 mL of buffer. These were immediately inserted into an NMR instrument and scans were taken at even time intervals to calculate the half-life of the compound based on integration. FIG. 12 shows an example of NMR in pH 5 acetate buffer at 25 degrees C.

Figure 6A:
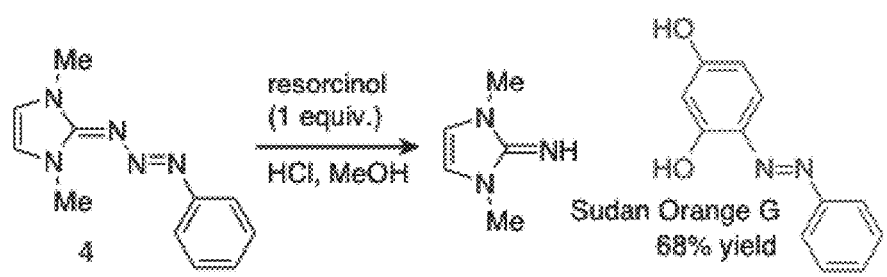

As another non-limiting example, an azide to NHC route may be used to synthesize triazabutadiene molecules (e.g., see FIG. 6H). For example, a triazabutadiene molecule was synthesized from dimethyl imidazole derived NHC and phenyl azide (see Compound 4 in FIG. 6A). Referring to FIG. 6A, when the triazabutadiene molecule (Compound 4) was treated with methanolic HCL, a rapid color change occurred. This change was confirmed to coincide with diazonium formation by trapping the reactive species with resorcinol to provide known diazo dye Sudan Orange G. When the triazabutadiene molecule (Compound 4) was treated with the much less acidic acetic acid, the same product was obtained. Compound 4 was not water-soluble.

Figure 6B:
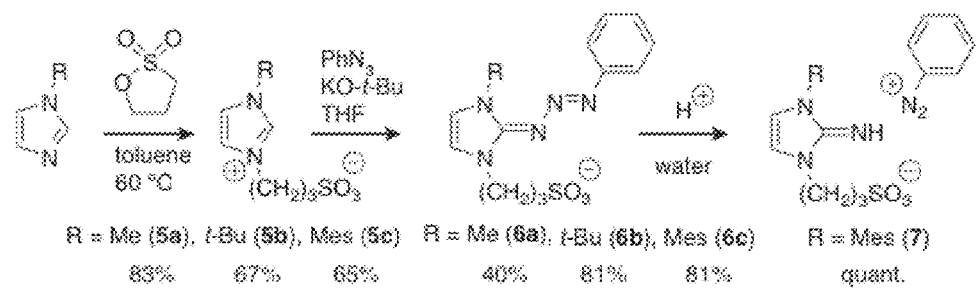

To render the triazabutadiene water-soluble, methyl imidazole was alkylated with propane sultone to provide the Zwitterionic NHC precursor Compound 5a (see FIG. 6B). Formation of the NHC under basic conditions in the presence of phenyl azide yielded the highly water soluble Compound 6a (see FIG. 6B). Compound 6a is highly colored, so its pH dependence was studied using UV/Vis. The reactions were not only pH-, but also scan-frequency dependent. Upon finding this, the stability of Compound 6a was studied in D2O in the dark using NMR. Even in the dark it was unstable, but not in the diazonium-forming way. Both Compound 6b and a more hindered mesityl (Mes) substituted Compound 6c (see FIG. 6B) were synthesized to stabilize what was initially considered to be a rearrangement pathway that could be blocked by steric repulsion. Compound 6c was the most stable of the three (less than 10% consumed after 24 hours versus 50% for Compound 6a and Compound 6b). It is not yet clear that the hypothesis of a simple rearrangement was correct. Dissolution in 0.1 N NaOH rendered all compounds stable (no detectable degradation after 24 hours in the dark).

As mentioned above, Compound 6c was reasonably stable in pure D2O. Upon adjusting the pH to 5 with HCl, a rapid initial consumption of Compound 6c to Compound 7 (see FIG. 6B) and a benzenediazonium salt was noted. After this initial burst of reactivity, a slowing and apparent arresting of the reaction was noted. At this pH the hydronium was the limiting reagent. All future reactions were run in buffers with a buffer capacity sufficient to maintain a large excess of hydronium ions. The experiments were performed in 90:10 H2O:D2O buffered solutions to minimize considerations of pH vs. pD. The decomposition to diazonium salts and Compound 7 was measured as a function of pH in phosphate/citrate buffers from pH 4-7 and in a phosphate buffer from pH 6-8. All runs provided linear correlations of concentration and time, indicating a pseudo-zero order reaction (first order with respect to hydronium ion with a large excess of hydronium ions). While the peaks for Compound 7 remained constant, the peaks associated with Compound 6c drifted downfield as the reaction progressed. This drifting was highly reproducible across samples and buffers, but the underlying cause is not understood at this time. A sigmoidal correlation between rate and buffer pH centered at pH 6 was obtained.

Figure 6C:
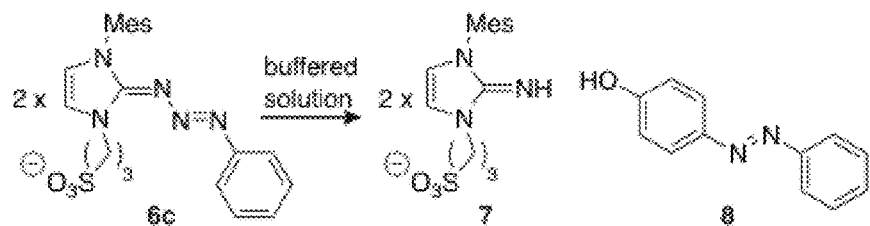
Figure 6D:
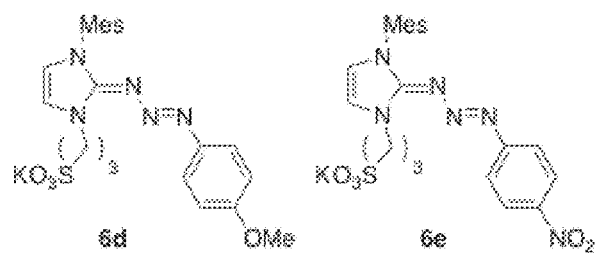

When resorcinol was not added to consume the diazonium species, 4-phenylazophenol (Compound 8) was observed (see FIG. 6c). Compound 8 came from the decomposition of one diazonium ion to phenol followed by reaction with a second diazonium ion. The instability of Compound 6c in a pH 7 phosphate buffer was surprising given the stability in D2O. Compound 6c was tested in a non-buffered 90:10 H2O:D2O solution and observed only >7% after 6 hours.

To further examine the reactivity of this class of compounds, variants Compound 6d and Compound 6e were synthesized (see FIG. 6c). It was hypothesized that the p-methoxy and p-nitro analogs (Compound 6d and Compound 6e, respectively) would display different reactivity profiles. It was observed that in pure D2O, 26% of Compound 6d was consumed after 24 hours in the dark at room temperature as compared with Compound 6e, which was stable to within the detection limit of NMR. Preliminary data shows that Compound 6d undergoes decomposition to the diazonium species more rapidly than Compound 6c in pH 5, 6, and 7 phosphate/citrate buffer (rates of 2.0×10-5, 1.0×10-5, and 0.53×10-5 M/s, respectively). Upon attempting the same study with Compound 6e it rapidly precipitated out of solution across the same pH range. After collecting the precipitate and dissolving it in deuterated methanol, no change was observed from a sample of Compound 6e that had never been exposed to a buffered solution. Treatment of this methanolic Compound 6e with HCl led to an immediate color change and diazonium formation was confirmed by trapping with resorcinol. It is possible that: 1) that the sodium salt of Compound 6e is much less soluble than the potassium salt; or 2) with different solvating ions present the sulfonate interacts with the electron-poor N2 nitrogen atom of the triazabutadiene to break conjugation and form an insoluble complex (this is backed by a reversible color change of the starting rust-red solid, to the light yellow precipitate). Note that the p-nitrobenzenediazonium salts are reported to have the best labeling efficiency of tyrosine residues on proteins.

The influence of solvated ions on reactivity will be studied. In water, or a heavy water/water mixture, a near-zero rate of diazonium salt formation was observed, yet in solutions buffered to pH 7 and even pH 7.4 an increase in the reaction rate was observed. It is possible that the ions in solution are somehow coordinating and facilitating the reaction. This could be a result of the anionic species or the cationic metal. To assess the role of the anionic component, the reaction in the presence of a range of buffers while holding the pH constant will be observed. Buffers that will be evaluated include but are not limited to those expected to have the most diverse properties, e.g., MES, a Zwitterionic morpholino sulfonic acid, and imidazolium chloride, the conjugate acid of a mild base, can both buffer a solution at pH 6.5, but ionic species in solution would be dramatically different. The metals in solution could well be acting as Lewis acids to activate our molecule. A range of metal halide salts dissolved in pure water at varying concentrations will be screened.

Figure 6E:
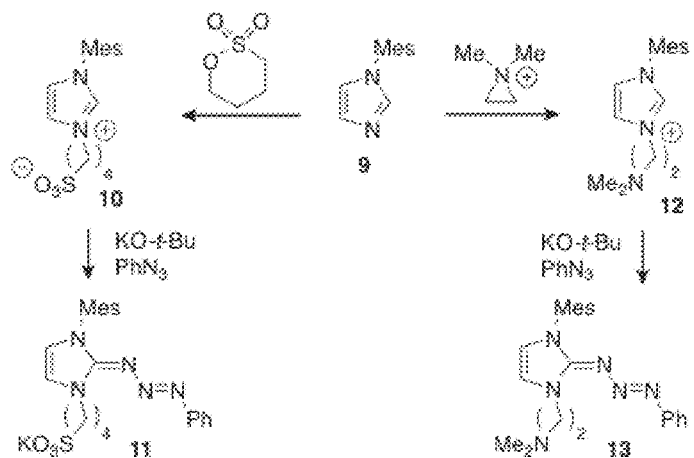

Note that all of the compounds in the 6 series (FIG. 6B, FIG. 6C, and FIG. 6D) have a built-in sulfonate to confer solubility. It is possible that this functional group could be serving an important role by effecting the localization of metals, directing them to interact with the nitrogen atoms of the triazabutadiene and thus alter the reactivity of the compound. This may be happening with Compound 6e to such an extreme that the compound is no longer soluble. This concept of a directed metal binding on triazabutadienes was observed, albeit in an organic environment. To study the role of the side chain, the imidazole core will be alkylated (see Compound 9 of FIG. 6E) with either butane sultone to provide imidazolium (Compound 10 of FIG. 6E) and triazabutadiene (Compound 11 of FIG. 6E), or a dialkyl aziridinium salt to provide the analogous Compound 12 and Compound 13 (see FIG. 6E) which invert the expected charge on the side-chain. The extra methylene in Compound 11 as compared with Compound 6 may alter the way that the side-chain bites back on the triazabutadiene. The tertiary amine will be protonated at physiological pH and as serve to invert the charge of the side arm. Without wishing to limit the present invention to any theory or mechanism, a potential bonus of Compound 13 is that the basic nitrogen may help localize this compound in the most acidic subcellular compartments much like LysoTracker™ dyes.

Regarding the role of mesityl group in reactivity, it is possible that a function of the mesityl in triazabutadiene reactivity is to provide a steric wall to prevent side reactions. It is not yet clear the extent to which the desymmeterization of the imidazole half affects the properties of the triazabutadienes. The NMR of Compound 6c (FIG. 6C) shows a tale of two hydrogen atoms on the imidazole ring. Without wishing to limit the present invention to any theory or mechanism, it is believed that because the ortho methyl groups prevent coplanar aryl rings, the mesityl group is unlikely to sit in conjugation with the imidazole, but the highly differentiated chemical environments might be explained by: 1) the mesityl n-system deshielding the adjacent hydrogen atom, and 2) the aryl ring having an inductive effect. Changing the p-methyl of the mesityl to electron donating and withdrawing groups may allow the adjustment of the electronic parameters without disrupting the steric bulk.

Figure 7A:
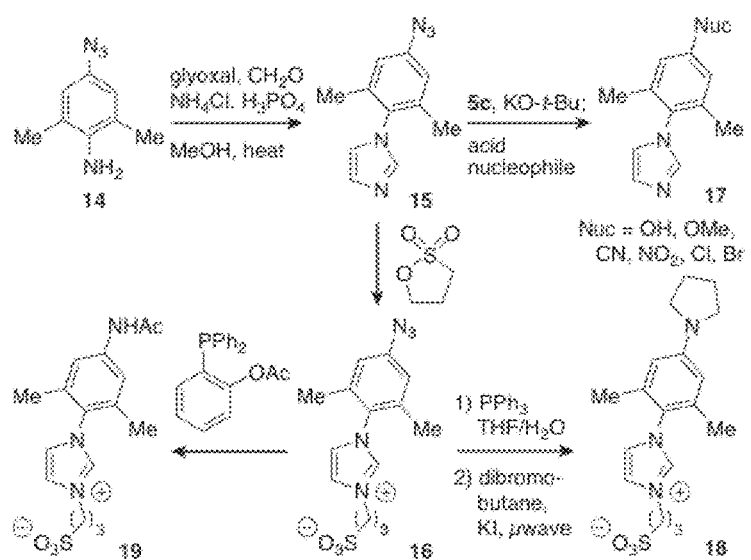
FIGS. 7A, 7B, 7C, and 7D show non-limiting examples of triazabutadienes.

Synthesis may be performed as shown below with known p-azido dimethyl aniline (Compound 14, see FIG. 7A) because it may lead to a wide range of substituted compounds. From imidazole (Compound 15, FIG. 7A) one can alkylate with 1,3-propanesultone to provide NHC precursor Compound 16 (FIG. 7A), or prior to that one can treat with an NHC to access the wealth of diazonium chemistry to provide Compound 17 (FIG. 7A) in all of its forms. Solvolysis in water or alcoholic solvent may provide a phenol or aryl ether, and copper mediated Sandmeyer-type chemistry may afford cyano, nitro or halogenated aryl species. From imidazolium Compound 16 Staudinger chemistry followed by aniline alkylation may provide Compound 18 (FIG. 7A), or traceless Staudinger-Bertozzi ligation may yield Compound 19 (FIG. 7A). These substrates cover a range of Hammett values while also providing an additional site of attachment to proteins, fluorophores, surfaces, etc.

Figure 7B:
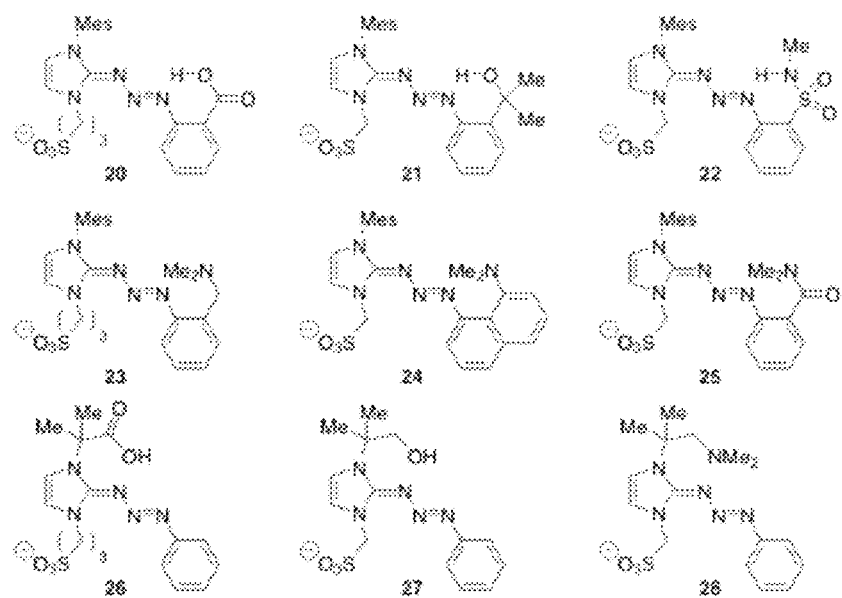

Regarding the role of intramolecular hydrogen bond acceptors/donors in reactivity, it may be possible to synthesize a series of triazabutadienes with hydrogen bond donors that possess a range of pKa values (Compounds 20-22, see FIG. 7B). In addition to H-bond donors, it may be possible to synthesize a series of internal bases (Compounds 23-25, see FIG. 7B). It may be possible that that bases positioned near the N1 nitrogen will favor protonation at N3 and thus make the triazabutadiene less stable to acidic media. These compounds are all synthetic targets given a strategy of coupling with aryl azides. The delicate triazabutadiene functional group is installed last under mild conditions.

Figure 7C:
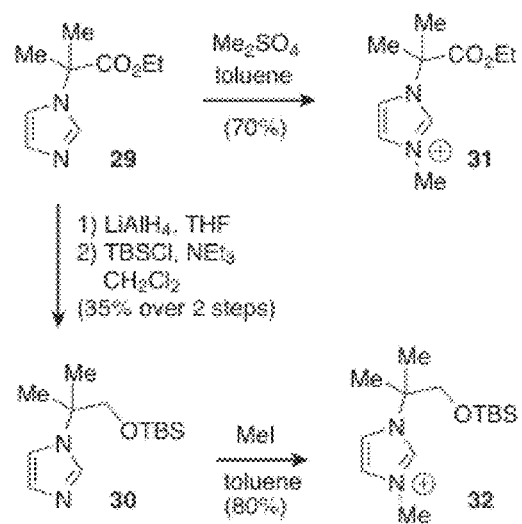

In addition to compounds that are designed to activate/deactivate the N1 nitrogen, it may be possible to synthesize a series of compounds where the N3 nitrogen in most likely to be affected (Compounds 26-28, FIG. 7B). An NHC with a hydrogen bond donor on a short arm was made. As in FIG. 7C, the synthesis of Compounds 26-28 from known Compound 29 may start with either alkylation to a compound like Compound 31 or reduction and protection to compound 30 followed by alkylation to Compound 32. If the mesityl is absolutely essential for a desired reactivity profile, a H-bond donor/acceptor may be inserted on a methyl group in the ortho position of the mesityl ring.

Figure 7D:
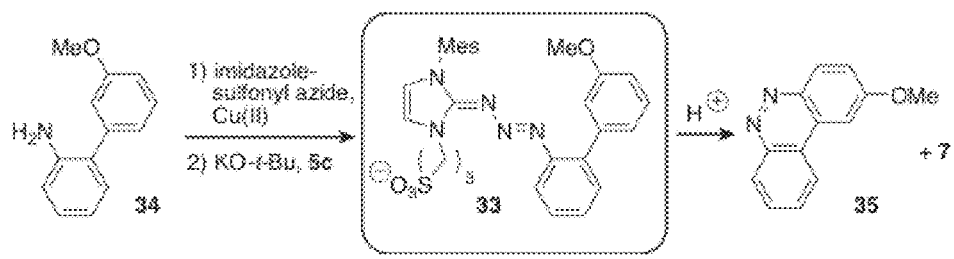

Regarding intramolecular trapping of diazonium species, it may be possible to synthesize triazabutadienes with adjacent functional groups that will rapidly consume the diazonium species. For example, Compound 33 (see FIG. 7D) contains an aryl ring, positioned ortho to the masked diazonium. The synthesis may start from a diazo transfer reaction to convert aniline Compound 34 (FIG. 7D) to an aryl azide. Coupling with Compound 5c (FIG. 6B) may complete the synthesis. It is possible that following diazonium unmasking an aromatic substitution reaction will occur to provide benzocinnoline Compound 35 (FIG. 7D). Because this reaction is intramolecular one might be able to use a non-activated ring, rendering the ring electron rich. The methy ether may serve as a site of attachment to chemical cargos. A second type of intramolecular diazonium trap that could be employed is a beta keto ester that is also ortho to the diazonium produced. Beta keto esters are known to react with diazonium species through enol form, and can generate oxo-cinnolines, which are biologically active cores.

IV. Applications and Methods of Use a. Diazonium Coupling Applications, Fluorogenic Applications, Etc.

The triazabutadiene molecules of the present invention may be utilized for a variety of purposes. For example, in some embodiments, the triazabutadiene molecules of the present invention are utilized for a chemoselectively-cleavable linkage for use in biological/complex settings where rapid, clean cleavage is of interest. In some embodiments, the triazabutadiene molecules are used for systems including but not limited to drug delivery systems, protein-protein interaction systems, pH environment detection systems, etc. Applications of these triazabutadienes may fall under one (or more) categories of reactivity (the present invention is not limited to these categories): a) diazonium salts as coupling partners; b) diazonium salts as surrogates for aryl cations.

Regarding diazonium coupling, the triazabutadiene molecules may be used for applications involving pH-dependent protein coupling. General examples involve methods for detecting protein-protein proximity or protein-protein interactions (in a sample). In some embodiments, the method comprises providing a first protein, wherein the first protein is conjugated with a triazabutadiene molecule according to the present invention. The first protein may be introduced to a sample. In some embodiments, the triazabutadiene molecule encounters a low pH in the sample; in some embodiments, acid is added to the sample to lower the pH appropriately. As previously discussed, in the low pH environment, the triazabutadiene molecule undergoes the irreversible reaction yielding the diazonium species and the cyclic guanidine species. As previously discussed, the diazonium species is adapted to react with a phenol group; thus if there is a nearby protein with a tyrosine residue, the diazonium species may react with it yielding an azo dye (e.g., Sudan Orange) that is visually distinct from the triazabutadiene molecule and the diazonium species. As such, detection of the azo dye (e.g., Sudan Orange) may be indicative of proximity or interaction of the first protein and the second protein.

In some embodiments, the method comprises introducing to the sample a first antibody specific for a first protein, wherein the first antibody is conjugated with a triazabutadiene molecule according to the present invention; and introducing to the sample a second antibody specific for a second protein, wherein the second antibody is conjugated with a phenol species (e.g., a p-nitrophenol moiety). In some embodiments, the method comprises introducing an acid to the sample to appropriately lower the pH of the sample. As previously discussed, in the low pH environment, the triazabutadiene molecule undergoes the irreversible reaction yielding the diazonium species and the cyclic guanidine species. As previously discussed, the diazonium species is adapted to react with a phenol group; thus if the phenol species (e.g., p-nitrophenol moiety) is nearby, the diazonium species may react with it yielding an azo dye (e.g., Sudan Orange) that is visually distinct from the triazabutadiene molecule and the diazonium species. As such, detection of the azo dye (e.g., Sudan Orange) may be indicative of proximity or interaction of the first protein and the second protein.

Figure 8A:
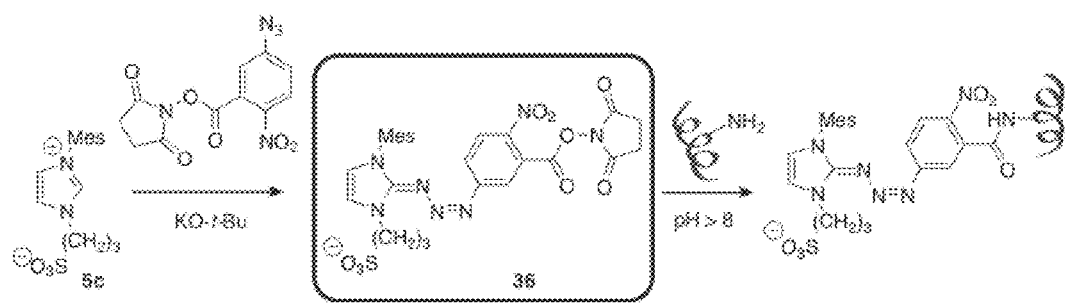
FIG. 8A shows an example of a triazabutadiene molecule adapted to modify a protein.

As a more specific example, the acid-labile reactivity may be used to assist in work deducing interaction partners between dengue virus (DENV) and endosomally localized host proteins. Upon endosomal acidification a viral-bound diazonium species may be unmasked and this may go on to react with Tyr-containing proteins that are associating with the virus. It is possible that this system could be used to trap an interaction that is relevant at a key point of viral entry, e.g., the fusion of membranes. Herein are non-limiting examples of synthesis of compounds that may be used in such systems, e.g., for modifying the viral surface. Lysine-reactive probes may be used to modify the surface of DENV proteins. Thus, by synthesizing triazabutadiene Compound 36 (see FIG. 8A) bearing an N-hydroxysuccinimide (NHS) ester it is possible to be able to couple the compound to one of many reactive Lys on the surface of DENV (see FIG. 8A). As previously discussed, a triazabutadiene molecule may be attached to a viral protein (e.g., a purified viral protein). Then, a system such as a cell line (e.g., mosquito cell line, human cell line, or even mosquitos themselves) may be infected with the viral protein. The infected system can be treated appropriately. The azo dye (e.g., Sudan Orange) may "label" any proteins that interact with or are nearby the viral protein (in the low pH environment). The present invention is not limited to this example.

Figure 8B:
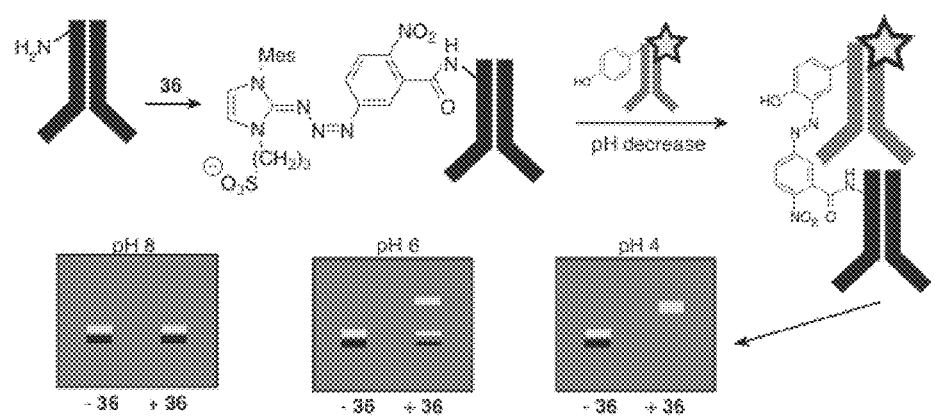
FIG. 8B shows an example of a triazabutadiene molecule conjugated to an antibody, wherein the conjugate is used for labeling a protein of interest.

Lys-NHS conjugation chemistry may work well on the basic side of neutral, which may be beneficial for our pH sensitive probes. Compound 36 (FIG. 8A, FIG. 8B) can be made in a straightforward fashion from NHC precursor Compound 5c (FIG. 6B) and an aryl azide. It is possible that the steric congestion about the NHC may favor the unencumbered azide over the potentially reactive NHS ester. If the NHS ester presents a problem during the synthesis it is possible to go into the reaction with a carboxylate instead and follow that by a coupling with N-hydroxysuccinimide. If electronically coupling the NHS ester to the aryl system is detrimental to reactivity it is possible to consider inserting an alkyl or, if needed for additional solubility, polyethylene glycol (PEG) linker. FIG. 8B shows a non-limiting example of a proof of concept system. Referring to FIG. 8B, a monoclonal antibody (e.g., mouse anti-biotin) may be modified with Compound 36. Once the surface is decorated with triazabutadienes, the extent of labeling may be quantified by coupling to resorcinol in a low pH solution and then analyzing the extent of modification by mass spectrometry. This may show the number of reactive triazabutadienes, and the presence of p-nitrophenol moieties may show the extent to which these fell apart prior to controlled acidification. Following this analysis, a fluorescent goat anti-mouse secondary antibody may be added, and then a gel-shift assay may be used to show that the two antibodies are covalently linked in a pH dependent manner.

In some embodiments, the triazabutadiene molecules of the present invention may be used in applications involving diazonium degradation to release cargo. For example, a group of applications takes advantage of the solvolysis of diazonium salts to produce phenolic byproducts. The degradation of diazonium salts to phenols, via aryl cations, is a first-order process that is not pH dependent in the physiological range of pHs. The half-life of this first order process depends on substitution on the aryl ring and the rate for benzenediazonium is ~4 hours. Indeed, the product of this degradation and subsequent azo-dye formation was observed if resorcinol is not put into the buffered NMR experiments.

In some embodiments, the acid-dependent instability of the triazabutadiene molecule may allow for a drug or cargo molecule to be deposited at a desired location and time (e.g., the reaction can be controlled and initiated at a desired time and location). As such, the present invention also features methods of delivering a drug (or a cargo compound) to a subject. In some embodiments, the method comprises providing a triazabutadiene molecule according to the present invention, conjugating a drug (or cargo compound) to the triazabutadiene molecule; and administering the conjugate (the drug/cargo-triazabutadiene conjugate) to the subject. In some embodiments, the method comprises providing a triazabutadiene molecule according to the present invention wherein the triazabutadiene molecule comprises the drug (or cargo compound); and administering the triazabutadiene molecule to the subject. In some embodiments, the diazonium species of the triazabutadiene molecule is part of the drug (or cargo compound). In some embodiments, the drug (or cargo compound) is formed when the diazonium species reacts to a phenol species. In some embodiments, the drug is an anti-cancer drug. The drug (or cargo compound) is not limited to an anti-cancer drug. Any appropriate drug for any appropriate condition may be considered. Likewise, the triazabutadiene molecules may be incorporated into drug/cargo-delivery systems for conditions including but not limited to cancer or other conditions associated with low pH states (e.g., gastrointestinal conditions, sepsis, ketoacidosis, etc.).

In some embodiments, drug delivery systems featuring triazabutadiene molecules may be enhanced with other reactions, e.g., enzymatic reactions. Such additional reactions may help provide appropriate specificity of the drug delivery system or appropriate timing to the drug delivery system.

Figure 9A:
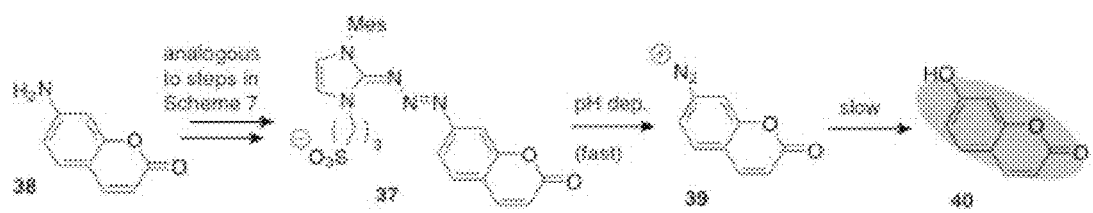
FIG. 9A shows an example of a fluorogenic triazabutadiene molecule.
Figure 9B:
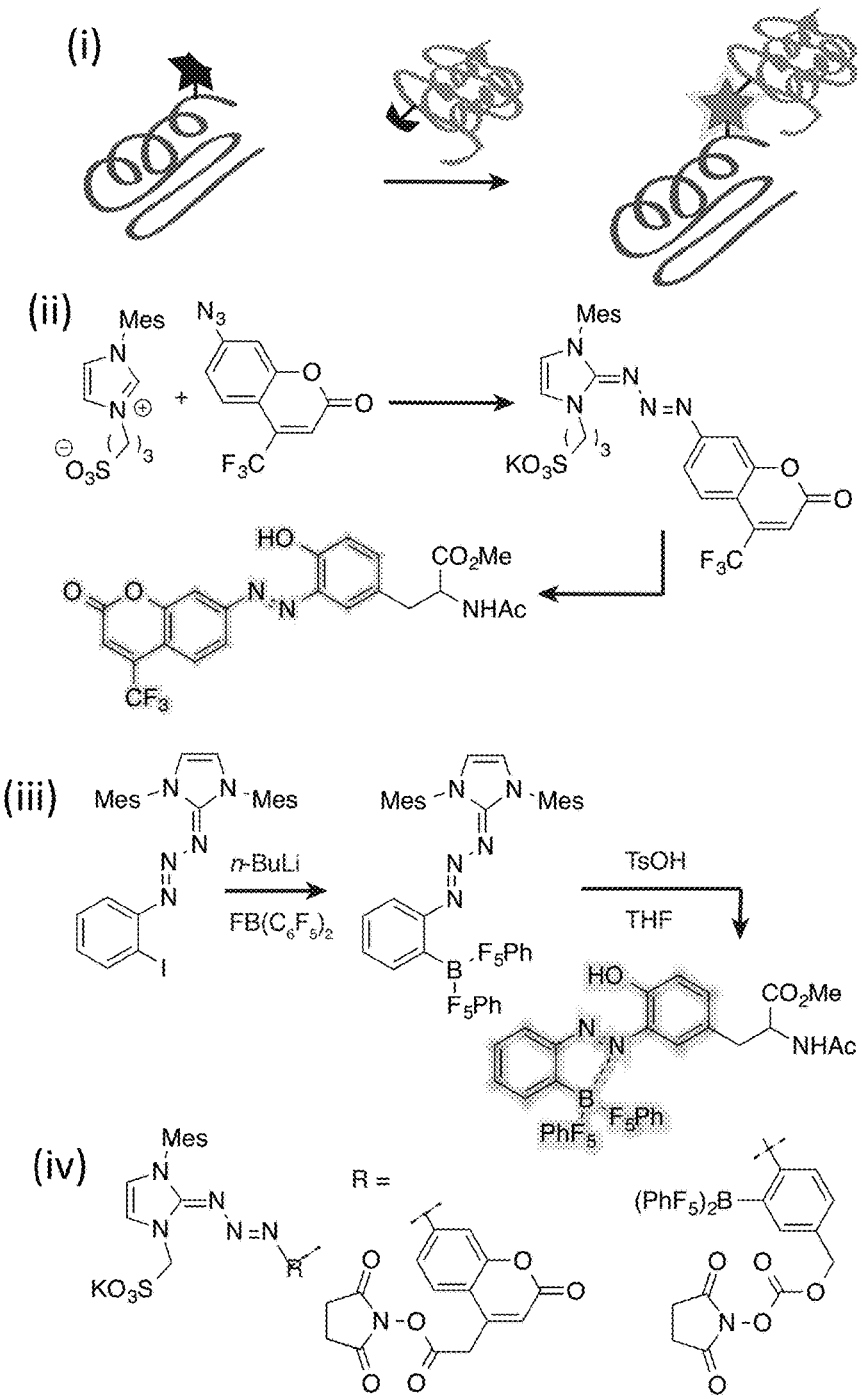
FIG. 9B shows a detailed reaction scheme involving a fluorogenic triazabutadiene molecule. For example, a triazabutadiene forms an aryl diazonium upon degradation. That aryl diazonium reacts with an electron rich aryl ring (e.g., tyrosine) and forms an azobenzene-containing fluorophore.

In some embodiments, the triazabutadiene molecules of the present invention may be used in applications involving fluorogenic molecules (e.g., see FIG. 9A, FIG. 9B). Fluorophores are highly sensitive to their aryl substituents and several classes rely on electron-donating functional groups at key locations to have reasonable quantum yields. Two of the best-studied fluorophore architectures where this is true are those derived from the xanthones (e.g., fluorescein and rhodamine-type dyes), and coumarins. It is possible that triazabutadienes may be significantly different in electronic properties compared with a simple phenol and as a result it is possible either a turn-on of fluorescence or a significant bathochromic shift upon formation of the phenol may result. It may be possible to synthesize triazabutadiene Compound 37 from 7-aminocoumarin (Compound 38) (see FIG. 9A). A diazotransfer reaction may provide a requisite aryl azide and coupling with NHC precursor Compound 5c (FIG. 6C) will yield a test compound. Once the pH drops it is possible that the resulting diazonium salt, Compound 39 (see FIG. 9A), may not be fluorescent until it further undergoes solvolysis in water to product coumarin Compound 40. If this derivative does not display desired properties, it is possible to turn to one of the xanthone cores. In addition to characterizing the UV/Vis of Compound 37, one may learn of its hydrolytic properties, including pH-dependent cleavage rate profile. Providing its properties make it adequate for studying a biological system as appropriate, one may synthesize an NHS- or maleimide-functionalized azido-coumarin to provide attachment chemistry. Such a dye may be used as a way of storing a molecular memory of past acidification. This may prove useful for a project where acidification, even during storage (e.g., DENV process), leads to a conformational change.

Figure 10A:
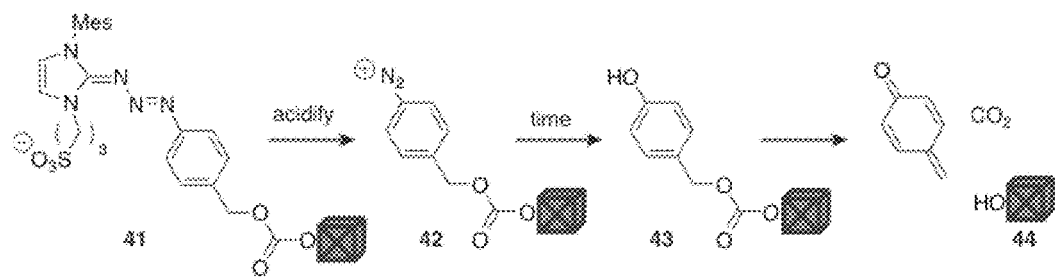
FIG. 10A shows an example of cargo release from a triazabutadiene molecule.

The present invention is not limited to the delivery of fluorophores and other phenolic derivatives. For example, the triazabutadiene molecules of the present invention may be used for applications involving benzoquinone methides. To expand the scope of chemical cargos that can be delivered using the triazabutadiene, it may be possible to synthesize derivatives that can undergo elimination via para-quinone methide chemistry (see FIG. 10A). Referring to FIG. 10A, after acidification, triazabutadiene Compound 41 may decompose to diazonium salt (Compound 42). This reactive species may decompose to a phenol (Compound 43), which itself decomposes to a quinone methide and may liberate the cargo molecule (Compound 44). It may be possible to modify the electronic properties of the central ring in order to influence the rates at each step. This system is may be useful for these modifications because none of them are expected to affect the cargo. The azide-coupling chemistry may render this amenable to wide variety of chemical cargos. In a biological context these compounds may be able to release their desired cargo upon entry into the endosome, or upon exposure to non-virally relevant acidic environments such as in proximity to cancerous tumors. This type of attachment chemistry may be utilized as a method for drug or detection delivery, and may have an added level of specificity if the system was delivered to a desired location using an antibody or aptamer.

Figure 10B:
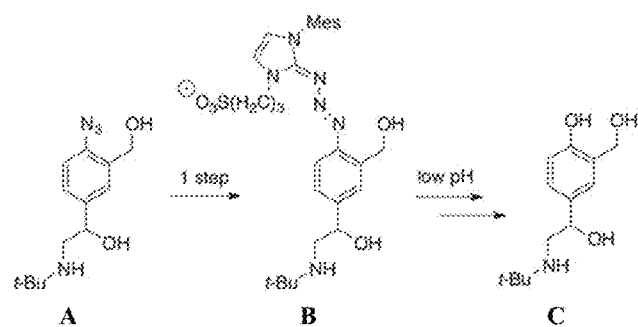
FIG. 10B shows an example of how a prodrug is released.
Figure 10C:
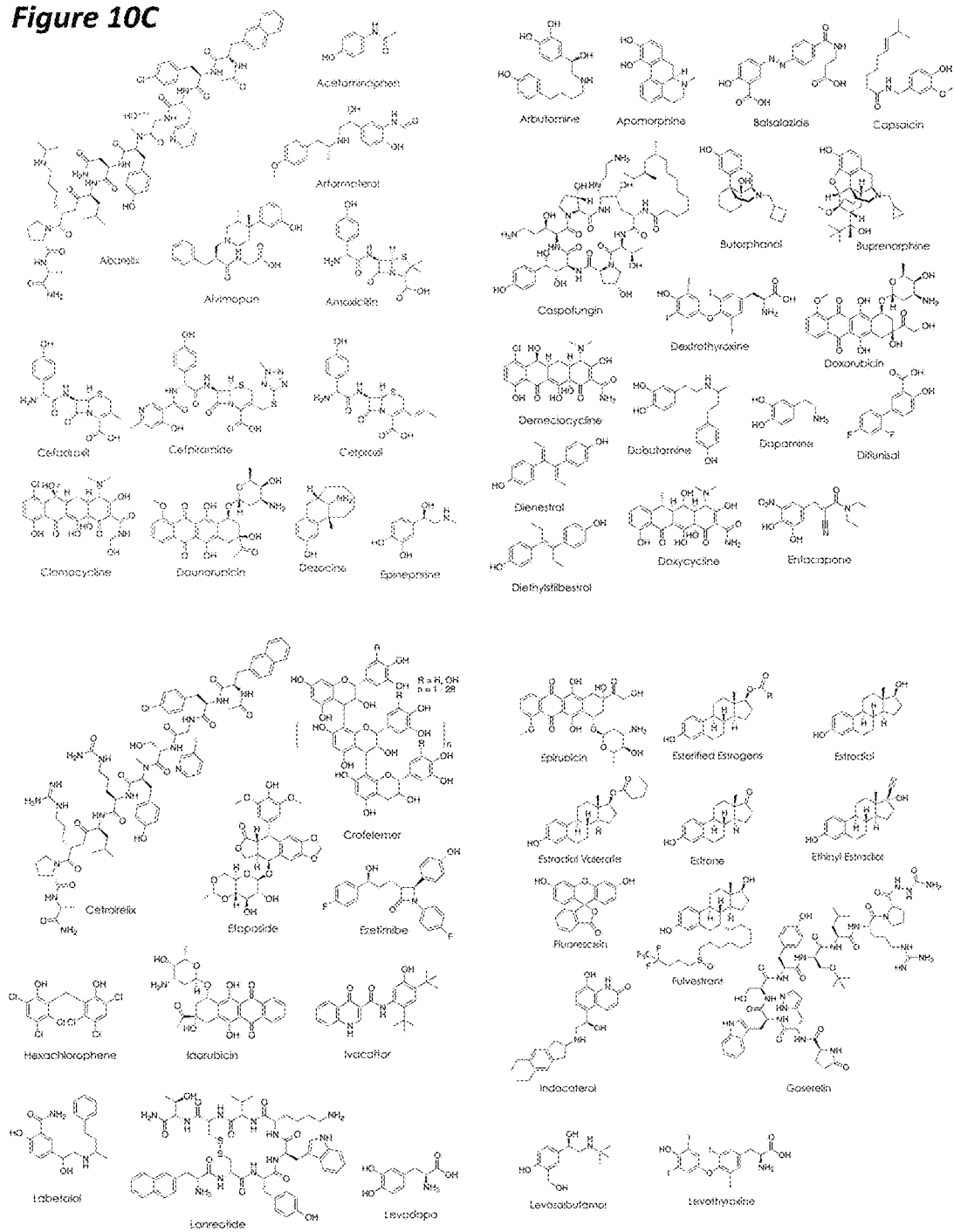
FIG. 10C shows non-limiting examples of drugs that have a phenolic functional group (which may be masked as prodrugs).

In some embodiments, $Z^1$ (see FIG. 1, FIG. 6I) is a prodrug comprising a phenolic functional group, wherein the phenolic group is masked as a triazylidene moiety. An example of how a prodrug is released (e.g., in an acidic environment, e.g., in a patient) is illustrated in FIG. 10B. Without wishing to limit the present invention to any theory or mechanism, it is believed that all drugs, such as those approved by the U.S. Food and Drug Administration, that have a phenolic functional group may be masked as a triazylidene moiety. Examples of drugs that can be masked as prodrugs are shown in FIG. 10C.

Figure 2B:
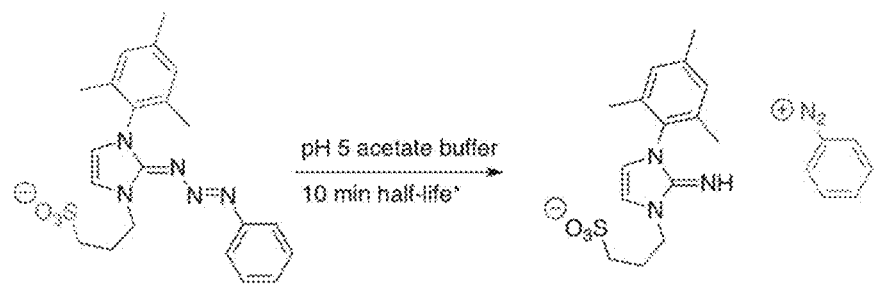
FIG. 2B shows a triazabutadiene molecule breaking down (in low pH conditions) to a diazonium species and a cyclic guanidine species.

Referring to FIG. 10B, Compound C is a stimulant that is produced by Glaxo Smith-Kline Beecham pharmaceutical company. The phenolic group of Compound C can be converted to an azide group, e.g., by displacement of the hydroxyl group with an azide group. In some embodiments, the phenolic group is first converted to a suitable leaving group before subjecting to a nucleophilic displacement reaction with an azide group. The resulting azide Compound A is then reacted with 3-(3-mesityl-2-(phenyltriaz-2-en-1-ylidene)-2, 3-dihydro-1H-imidazol-1-yl) propane-1-sulfonate to produce triazylidene Compound B. In some embodiments, when Compound B is administered to a patient (e.g., orally or intravenously), the acidic environment of the patient's gastrointestinal tract (if administered orally) or patient's blood plasma (when administered intravenously) decomposes it to generate a corresponding diazonium compound (FIG. 2B) regenerates the phenolic group as illustrated in FIG. 10B. By converting the phenolic group (e.g., the hydroxyl group that is attached to a phenyl ring) to an azide, one skilled in the art having read the present application can readily convert the phenol compound to a triazylidene compound of the invention. Thus, the triazylidene moiety serves as a masking group for a phenolic functional group.

The present invention also features a method for administering a drug comprising a phenolic function group to a subject in need of such a drug administration. In some embodiments, the method comprises converting a drug comprising a phenolic-functional group to a prodrug, wherein said prodrug comprises an acid labile triazylidene moiety, and administering said prodrug to a subject in need of such a drug administration. In some embodiments, the triazylidene compound may also comprise a water solubility conferring moiety and/or $Y^1$ functional group defined in FIG. 1.

The present invention also features a method of converting a drug comprising a phenolic-function group to an acid labile prodrug. In some embodiments, the phenolic-functional group is converted to an azide group. The azide functional group may then be reacted with a carbene to produce an acid labile prodrug comprising a triazylidene moiety (see FIG. 6J).

In some embodiments, a triazabutadiene molecule is conjugated to another molecule (a conjugate molecule), e.g., a protein (e.g., an amino acid such as but not limited to lysine), a lipid, or other appropriate molecule. In some embodiments, the diazonium species part of the triazabutadiene molecule is conjugated to the conjugate molecule. In some embodiments, the cyclic guanidine species part of the triazabutadiene molecule is conjugated to the conjugate molecule. In some embodiments, the triazabutadiene molecule is attached to the conjugate molecule via a linker. Linkers are well known to one of ordinary skill in the art and may include (but are not limited to) a polyether linkers such as polyethylene glycol linkers. In some embodiments, the conjugate molecule to which the triazabutadiene molecule is conjugated comprises an antibody or a fragment thereof. In some embodiments, the conjugate molecule to which the triazabutadiene molecule is conjugated comprises a viral protein, e.g., a viral protein of dengue virus (DENV).

In some embodiments, the triazabutadiene molecules of the present invention are used for pull-down studies wherein a biomolecule or protein of interest is attached to one side and the other side is appended to something such as but not limited to a small molecule (e.g., hapten such as biotin) or compound. Using biotin as an example, the biomolecule or protein of interest can be pulled down using an avidin bead (which binds strongly to the biotin) and thoroughly washed.

This may be useful for protein enrichment. The biomolecule or protein of interest may then be cleaved from the avidin bead by means of reductive cleavage of the triazabutadiene that holds them together. The present invention is not limited to these components, for example this application could also feature the use of a probe (e.g., fluorescent or otherwise) attached to an antibody used to interrogate a complex sample.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

As previously discussed, the diazonium species can react with a phenol species such as resorcinol or other appropriate phenol species. In some embodiments, a phenol species or resorcinol species is conjugated to a protein, e.g., a protein different from the protein to which the triazabutadiene molecule is conjugated, a protein that is the same protein to which the triazabutadiene molecule is conjugated, etc. In some embodiments, the resorcinol species or phenol species that the diazonium species reacts with is the phenol functional group of a tyrosine residue.

The present invention also features a method of detecting an environment having a low pH. In some embodiments, the method comprises providing a sample (e.g., tissue sample, cell sample, any appropriate sample) and introducing a triazabutadiene molecule according to the present invention to the sample. An environment having a low pH (a low pH appropriate for the triazabutadiene molecule) causes the triazabutadiene molecule to break down into a diazonium species and a cyclic guanidine species. Since the diazonium species is visually distinct from the triazabutadiene, visualization of the diazonium species is indicative of the low pH environment. In some embodiments, the method further comprises introducing a resorcinol species or a phenol species to the sample. The resorcinol species or phenol species may react with the diazonium species to form an azo dye. Since the azo dye is visually distinct from the diazonium species and the triazabutadiene species, detection of the diazonium species and/or the azo dye would be indicative of the low pH environment.

The present invention is not limited to the methods and uses described herein. For example, in some embodiments, the triazabutadiene molecules are used as reagents in buffers for various chemical or biochemical assays (e.g., immunohistochemistry assays, in situ hybridization assays, protein assays such as western blots, ELISAs, etc.).

b. Adhesive Applications

In some embodiments, the triazabutadiene molecules of the present invention are used for adhesive applications. For example, the present invention features underwater adhesive compounds derived from triazabutadiene molecules (and from reaction products of triazabutadienes), methods of use of said triazabutadiene molecules and underwater adhesives, and methods of underwater adhesion. For example, the adhesives of the present invention may be used for a variety of applications such as marine technologies (e.g., boats, buoys, jet skis, etc.), surgical mesh, medical devices, swimming pools, or any other appropriate environment. The present invention is not limited to the methods and uses described herein.

The triazabutadiene molecules may function as masked compounds that, when exposed to water, form reaction products that form covalent bonds with surfaces containing phenols. Without wishing to limit the present invention to any theory or mechanism, it is believed that the system and methods of the present invention are advantageous because the technology provides underwater adhesion, the adhesive bond may be colored (e.g., highly colored azobenzene linkages), which may serve as a positive indicator that the desired reaction has occurred; and/or the chemical compounds (e.g., unreacted diazonium species) may degrade over time so that the unbonded surface does not remain sticky (e.g., adapted for adhesion) permanently.

Figure 11:
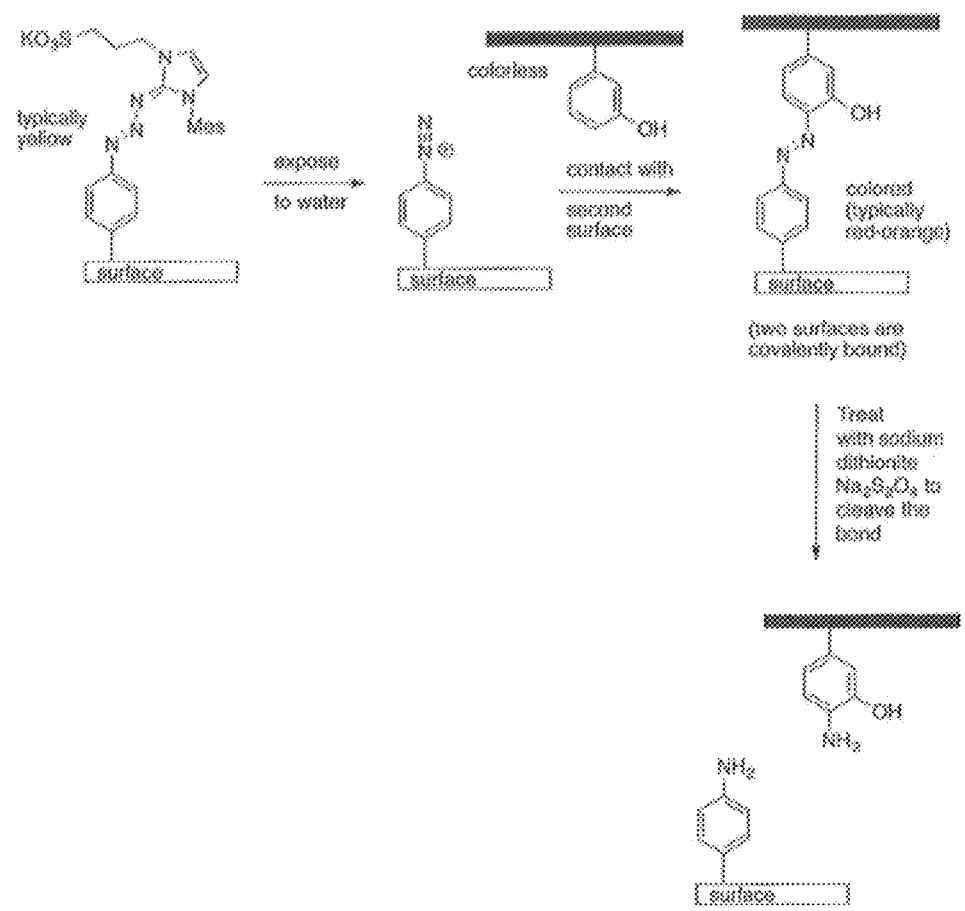
FIG. 11 shows an example of triazabutadiene molecules used as adhesives.

FIG. 11 shows a triazabutadiene molecule bonded to a first surface. A phenol-containing compound is bonded to a second surface. First and/or second surfaces may include but are not limited to glass, plastic, a biomaterial, or any other appropriate surface, e.g., a surface that allows for linkage chemistry, e.g., the first surface could be any surface that allows for the attachment of a triazabutadiene molecule, the second surface could be any surface that allows for the attachment of a phenol-containing compound. Non-limiting examples of materials also include Tufnol materials such as phenolic cotton laminated plastics, phenolic paper laminated plastics, etc., a phenol formaldehyde resin such as bakelite (or bakelite), etc.

As in FIG. 11, the first reaction (wherein the triazabutadiene molecule is exposed to water to result in diazonium species formation) may be performed at room temperature; however, the reaction may be at a different temperature, e.g., depending on the environmental conditions. Without wishing to limit the present invention to any theory or mechanism, it is believed that different temperatures may affect the rate at which the first reaction (wherein the triazabutadiene molecule is exposed to water to result in diazonium species formation) and/or the second reaction (wherein the diazonium species reacts with the phenol-containing compound on the second surface) occurs.

In some embodiments, the covalent bond formed between the phenol-containing compound and the diazonium compound forms a colored compound. In some embodiments, the color is red, orange, or a mix of red and orange. In some embodiments, the formation of the color can be used as a positive indicator that the bonding reaction has occurred.

The diazonium species, if not reacted with the phenol-containing compound, can break down into a phenolic compound (e.g., the diazonium species will extrude nitrogen gas to generate an aryl cation that will rapidly be quenched by solvating water, thus generating the phenolic compound). This reaction is typically much slower than the second reaction (wherein the diazonium species reacts with the phenol-containing compound bound to the second surface). This phenomenon can allow for the unreacted diazonium species to eventually become non-sticky, or unreactive, which may be beneficial in certain circumstances (e.g., see photolithography below).

FIG. 11 also shows cleavage of the azobenzene linkage upon treatment with the reducing agent sodium dithionite. Thus, the present invention also features cleaving the bonded surfaces using a reducing agent such as sodium dithionite. In some embodiments, the reducing agent is not sodium dithionite but is another appropriate reducing agent.

In some embodiments, the reaction of the triazabutadiene molecule to the diazonium species occurs in water within 10 seconds minutes. In some embodiments, the reaction of the triazabutadiene molecule to the diazonium species occurs in water within 30 seconds minutes. In some embodiments, the reaction of the triazabutadiene molecule to the diazonium species occurs in water within 1 minute. In some embodiments, the reaction of the triazabutadiene molecule to the diazonium species occurs in water within 5 minutes. In some embodiments, the reaction of the triazabutadiene molecule to the diazonium species occurs in water within 10 minutes. In some embodiments, the reaction of the triazabutadiene molecule to the diazonium species occurs in water within 15 minutes. In some embodiments, the reaction of the triazabutadiene molecule to the diazonium species occurs in water within 20 minutes. In some embodiments, the reaction of the triazabutadiene molecule to the diazonium species occurs in water within 25 minutes. In some embodiments, the reaction of the triazabutadiene molecule to the diazonium species occurs in water within 30 minutes. In some embodiments, the reaction of the triazabutadiene molecule to the diazonium species occurs in water within 45 minutes. In some embodiments, the reaction of the triazabutadiene molecule to the diazonium species occurs in water within 60 minutes.

In some embodiments, the triazabutadiene molecule has a half-life of no more than 1 hour in a pH 7.4 aqueous solution. In some embodiments, the triazabutadiene molecule has a half-life of no more than 30 minutes in a pH 7.4 aqueous solution. In some embodiments, the triazabutadiene molecule has a half-life of no more than 15 minutes in a pH 7.4 aqueous solution.

In some embodiments, the bonding of the diazonium species to the phenol-containing compound occurs in water within 10 seconds. In some embodiments, the bonding of the diazonium species to the phenol-containing compound occurs in water within 30 seconds. In some embodiments, the bonding of the diazonium species to the phenol-containing compound occurs in water within 1 minute. In some embodiments, the bonding of the diazonium species to the phenol-containing compound occurs in water within 5 minutes. In some embodiments, the bonding of the diazonium species to the phenol-containing compound occurs in water within 10 minutes. In some embodiments, the bonding of the diazonium species to the phenol-containing compound occurs in water within 15 minutes. In some embodiments, the bonding of the diazonium species to the phenol-containing compound occurs in water within 20 minutes. In some embodiments, the bonding of the diazonium species to the phenol-containing compound occurs in water within 25 minutes. In some embodiments, the bonding of the diazonium species to the phenol-containing compound occurs in water within 30 minutes. In some embodiments, the bonding of the diazonium species to the phenol-containing compound occurs in water within 45 minutes. In some embodiments, the bonding of the diazonium species to the phenol-containing compound occurs in water within 60 minutes.

In some embodiments, light can be used to speed up the reaction. In some embodiments, varying triazabutadienes amounts can be added to speed up or slow down the reaction. In some embodiments, a surplus of triazabutadienes may be used, which may help allow for an amount of triazabutadiene molecules that are unreacted (and those unreacted triazabutadienes may be buried amongst other reacted compounds). These unreacted triazabutadienes that are buried may be useful in the event of a break in the seal. For example, a break in the seal may cause water to then react with the unreacted triazabutadiene molecules to yield the diazonium species, and those newly formed diazonium species can then subsequently bond to nearby phenol-containing compounds to perhaps "heal" the break in the seal.

In some embodiments, the surface (e.g., glass, plastic, etc.) is modified, e.g., using an etching mechanism. In some embodiments, photolithography etching may be used to shape the available triazabutadiene molecules. For example, one may intentionally expose certain triazabutadiene molecules to light (e.g., in a pattern via a mask, for example) so as to transition them to the diazonium species; if left unreacted, the diazonium species will then transition to a phenolic compound (as previously described), and thus will be non-sticky or unreactive with the phenol-containing compound on a second surface. This system can allow for the etching away of undesired triazabutadienes.

The present invention features adhesive systems. In some embodiments, the system comprises a first surface (e.g., glass, plastic, the like, or a combination thereof), wherein the first surface is at least partially coated with a triazabutadiene molecule according to the present invention or at least partially coated with a diazonium species derived from a triazabutadiene molecule according to the present invention. The system may further comprise a second surface (e.g., glass, plastic, the like, or a combination thereof), wherein the second surface is at least partially coated with a phenol species (e.g., a resorcinol species, a phenol species, another electron rich aromatic that can undergo diazonium chemistry, the like or a combination thereof). In the case of a triazabutadiene molecule bonded to the first surface, the triazabutadiene molecule may then undergo a reaction (e.g., in water) to yield a diazonium species. In some embodiments, when the first surface is contacted with the second surface, a covalent bond is formed between the diazonium species and the phenol species (e.g., a resorcinol species, a phenol species, another electron rich aromatic that can undergo diazonium chemistry, the like or a combination thereof) so as to bond the first surface to the second surface. In some embodiments, the system is adapted to form the covalent bond in aqueous (e.g., water) conditions. In some embodiments, both surfaces are coated with the triazabutadiene and the coupling occurs after some have undergone conversion to phenol via diazonium species.

The present invention also features adhesive kits. In some embodiments, the kit comprises a first surface (e.g., glass, plastic, the like, or a combination thereof), wherein the first surface is at least partially coated with a triazabutadiene molecule according to the present invention or the first surface is at least partially coated with a diazonium species derived from a triazabutadiene molecule according to the present invention. The system may further comprise a second surface (e.g., glass, plastic, the like, or a combination thereof), wherein the second surface is at least partially coated with a resorcinol species, a phenol species, another electron rich aromatic that can undergo diazonium chemistry, or a combination thereof. In some embodiments, when the first surface is treated with water, the diazonium species is exposed on the first surface (unless the first surface already has the diazonium species). In some embodiments, when the first surface is contacted to the second surface, a covalent bond is formed between the diazonium species and the resorcinol or phenol species or electron rich aromatic so as to bond the first surface to the second surface. In some embodiments, the kit further comprises water for treating the triazabutadiene molecules on the first surface so as to yield diazonium species on the first surface.

The present invention also features a method of bonding a first surface to a second surface. In some embodiments, the method comprises providing the first surface (e.g., as described above), wherein the first surface is at least partially coated with a triazabutadiene molecule or diazonium species according to the present invention, and providing the second surface (e.g., as described above), wherein the second surface is at least partially coated with a phenol species (e.g., a resorcinol species, a phenol species, another electron rich aromatic that can undergo diazonium chemistry, or a combination thereof, etc.). In the case of triazabutadiene molecules bonded to the first surface, the method may further comprise treating the triazabutadiene molecules of the first surface with an acid to yield a diazonium species. In some embodiments, the molecules of the first surface are treated with water to yield a diazonium species. In some embodiments, the first surface is then contacted to the second surface. A covalent bond is formed (e.g., in aqueous, water conditions) between the diazonium species and the phenol species so as to bond the first surface to the second surface. In some embodiments, the step of contacting the first surface to the second surface is done in aqueous conditions.

In some embodiments, the triazabutadiene molecule (or a diazonium species) is conjugated to a molecule other than a glass or plastic as described above. In some embodiments, the triazabutadiene molecule (or a diazonium species) is conjugated to a surface via a linker. Linkers are well known to one of ordinary skill in the art and may include (but are not limited to) a polyether linkers such as polyethylene glycol linkers.

The present invention is not limited to the methods and uses described herein. For example, in some embodiments, the triazabutadiene molecules are used as reagents in buffers for various chemical or biochemical assays (e.g., immunohistochemistry assays, in situ hybridization assays, protein assays such as western blots, ELISAs, etc.).

The disclosures of the following documents are incorporated in their entirety by reference herein: U.S. Pat. No. 8,617,827; U.S. Pat. Application No. 2009/0048222; U.S. Pat. No. 3,591,575. U.S. Pat. No. 3,607,542; U.S. Pat. No. 4,107,353; WO Pat. No. 2008090554; U.S. Pat. No. 4,218,279; U.S. Pat. App. No. 2009/0286308; U.S. Pat. No. 4,356,050; U.S. Pat. No. 8,603,451; U.S. Pat. No. 5,856,373; U.S. Pat. No. 4,602,073; U.S. Pat. No. 3,959,210. The disclosures of the following publications are incorporated in their entirety by reference herein: Kimani and Jewett, 2015, Angewandte Chemie International Edition (DOI: 10.1002/anie.201411277—Online ahead of print). Zhong et al., 2014, Nature Nanotechnology 9, 858-866; Stewart et al., 2011, J Polym Sci B Polym Phys 49(11):757-771; Poulsen et al., 2014, Biofouling 30(4):513-23; Stewart, 2011, Appl Microbiol Biotechnol 89(1):27-33; Stewart et al., 2011, Adv Colloid Interface Sci 167(1-2):85-93; Hennebert et al., 2015. Interface Focus 5(1):2014.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A water-soluble triazabutadiene molecule having a structure of any one of the following:

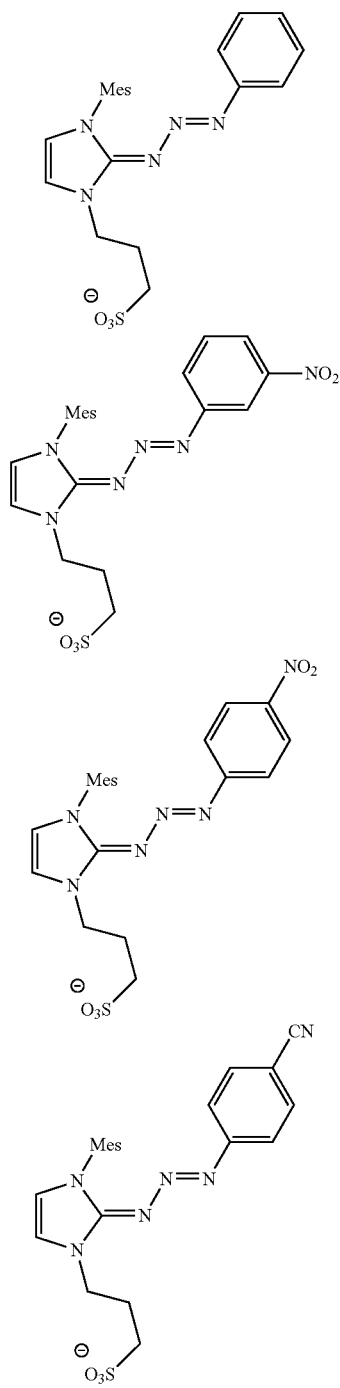

27
-continued
28
-continued
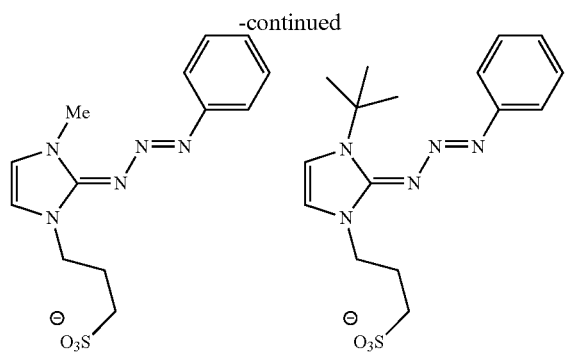
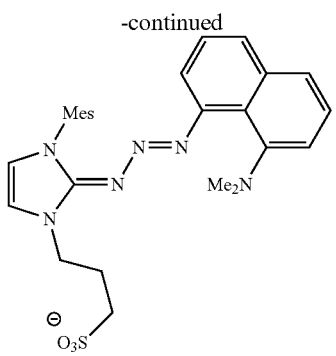
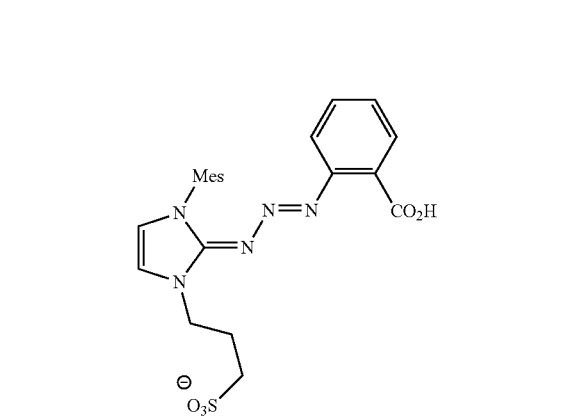
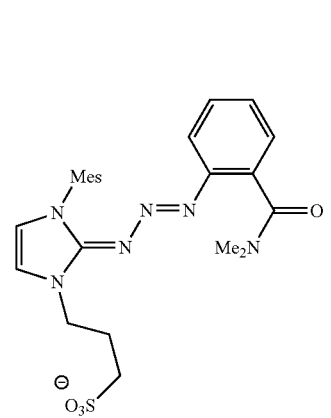
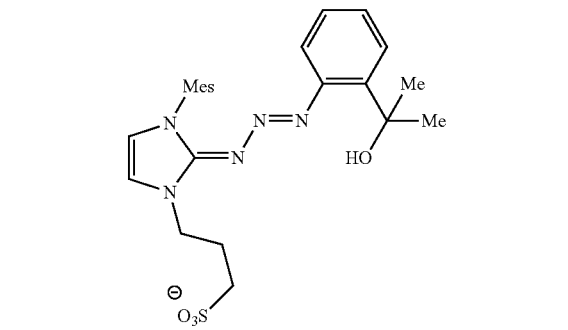
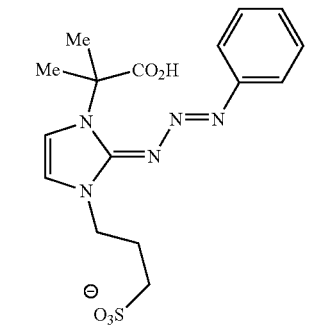
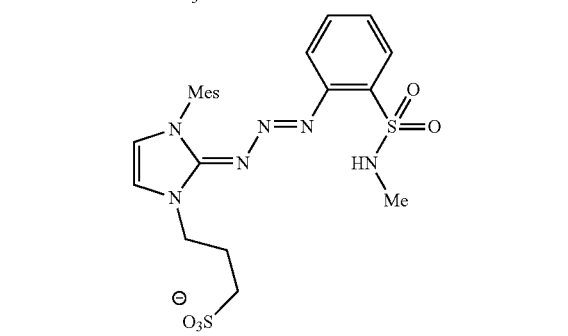
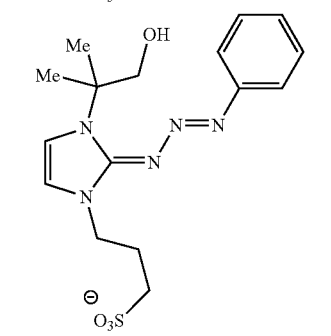
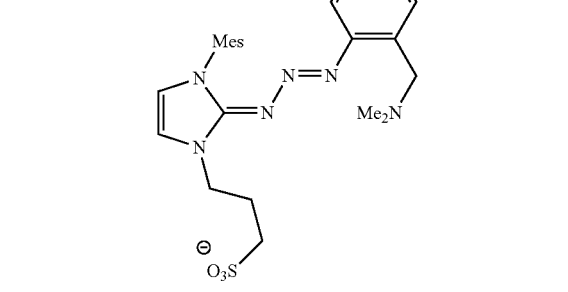
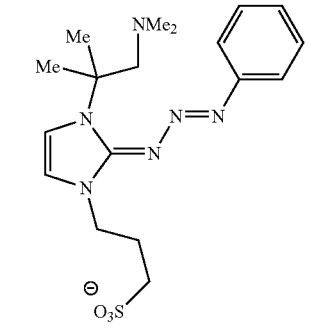

-continued

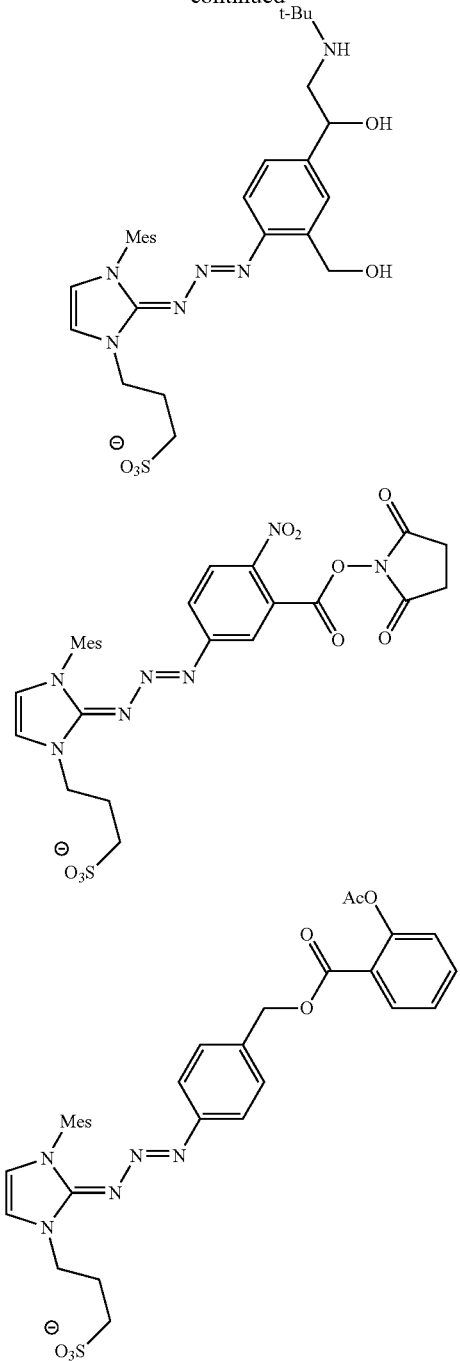

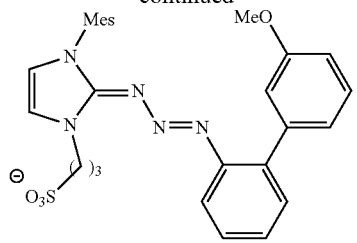

wherein Me is methyl, Mes is 2, 4, 6-trimethylbenzene, and t-Bu is tert-butyl.

2. The triazabutadiene molecule of claim 1, wherein the molecule has half-life of at least 12 hours in a pH 7.4 buffer.

3. The triazabutadiene molecule of claim 1, wherein the triazabutadiene molecule breaks down to a diazonium species and a cyclic guanidine species.

4. The triazabutadiene molecule of claim 3, wherein breaking down of the triazabutadiene occurs in a pH of 7.0 or less, a pH of 6.0 or less, or a pH of 5.0 or less.

5. The water-soluble triazabutadiene molecule of claim 1, wherein the triazabutadiene molecule breaks down in reducing conditions yielding an aniline and a hydrazine, or a urea functionality and a terminal aryl triazene.

6. The triazabutadiene molecule of claim 3, wherein breaking down of the triazabutadiene occurs when the triazabutadiene molecule is subjected to light.

7. The triazabutadiene molecule of claim 6, wherein the light has a wavelength from 340 nm to 420 nm.

8. The triazabutadiene molecule of claim 3, wherein the diazonium species reacts with an electron rich aromatic to produce a product species.

9. The triazabutadiene molecule of claim 8, wherein the electron rich aromatic comprises a resorcinol species or a phenol species.

10. The triazabutadiene molecule of claim 9, wherein the phenol species is that of a tyrosine molecule.

11. The triazabutadiene molecule of claim 1, wherein the molecule is conjugated to a protein.

12. The triazabutadiene molecule of claim 8, wherein the product species comprises an aryl azo dye.

13. The triazabutadiene molecule of claim 1, wherein the molecule is conjugated to a surface.

* * * * *